United States Patent
Nishikawa et al.

(10) Patent No.: US 7,202,083 B1
(45) Date of Patent: Apr. 10, 2007

(54) PLANT PROMOTERS AND PLANT TERMINATORS

(75) Inventors: Satomi Nishikawa, Ashiya (JP); Kenji Oeda, Kyoto (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/806,197

(22) PCT Filed: Sep. 28, 1999

(86) PCT No.: PCT/JP99/05303

§ 371 (c)(1),
(2), (4) Date: Mar. 27, 2001

(87) PCT Pub. No.: WO00/20613

PCT Pub. Date: Apr. 13, 2000

(30) Foreign Application Priority Data

Oct. 2, 1998 (JP) ................... 10-281124

(51) Int. Cl.
*C12N 5/14* (2006.01)
*C12N 1/21* (2006.01)
*C12N 15/82* (2006.01)
*C12N 15/74* (2006.01)
*C12N 15/00* (2006.01)
*C07H 21/04* (2006.01)

(52) U.S. Cl. .................... 435/419; 435/252.3; 435/468; 435/471; 435/476; 435/320.1; 536/24.1; 536/23.1

(58) Field of Classification Search ............... 536/24.1, 536/23.4; 435/69.1, 320.1, 468, 410, 252.3; 800/278
See application file for complete search history.

(56) References Cited

U.S. PATENT DOCUMENTS 5,352,605 A    10/1994  Farley et al.
5,959,176 A  *  9/1999  Torikai et al.

FOREIGN PATENT DOCUMENTS

EP    0 659 884 A2    6/1995
EP    0 824 150 A2    2/1998

OTHER PUBLICATIONS

Database GenEMBL. Accession No. AR076817. Sequence 2 from USP 5,959,176 to Torikai et al, published Sep. 1999. Accessed Sep. 23, 2002.*
Database GenEMBL, Accession No. AR076817, Sequence 2 from USP 5,959,176 to Torikai et al., Published Sep. 1999, Accessed Sep. 23, 2002.

* cited by examiner

*Primary Examiner*—Nancy Vogel
(74) *Attorney, Agent, or Firm*—Fitch, Even, Tabin & Flannery

(57) ABSTRACT

Promoters capable of efficiently expressing a gene of interest in plants include (1) either a DNA containing SEQ ID No:1 or SEQ ID No:7, or a biological functional equivalent DNA containing SEQ ID No:1 or SEQ ID No:7 that have modifications in their respective nucleotide sequence provided that each retains more than 90% identity to the nucleotide sequence of any region containing at least 250 bp within SEQ ID No:1 or SEQ ID No:7, respectively. Terminators capable of efficiently expressing a gene of interest in plants include either a DNA containing SEQ ID No:2, or a biological functional equivalent DNA containing a SEQ ID No:2 that has a modified nucleotide sequence provided that it retains more than 90% identity to the nucleotide sequence of any region containing at least 250 bp within SEQ ID No:2.

21 Claims, 4 Drawing Sheets

SEQUENCE LISTING

<160> NUMBER OF SEQ ID NOS: 29

<210> SEQ ID NO 1
<211> LENGTH: 2052
<212> TYPE: DNA

<213> ORGANISM: Daucus carota

<400> SEQUENCE: 1

```
catgtgtgcc ctacagcaca tagggcctgt ttggttgaga gaagcagaag ctgcttctga      60
cttcttcttc ttttgacctg tttgtataaa gaagtagaaa tatttttaaa aagctgcgaa     120
tactaacttc tctctcacaa cttccgcttc ttttccaaac actttattaa cttttttact     180
tctcatttct actccacttc tttgctataa gcaagaaatc acttctttta agctaacccca    240
aacggcctca ataaaagatc attcataaat gtatctttca attttaggat aacaatacgt     300
gaacagggtt atttttttaac gtgtcaacaa attctaataa ttttacctgg ccggtgaaca    360
ccgtcttcca agataatata ttttaatttt gtagcctccc ttttaaccaa attcgcatgc     420
aggacgactt aggtgaatac acattgtact gtgagtcttt aaacaaagaa caagtggttc     480
atgctcagcc atcaaaattg acaaaacccg acacaacact ctatccacgt actatacttt     540
tggccgaatg cttctcaaaa tgttttttat atgtaaaata atgcccatcc aaggataagt     600
aaaattcccg tttaaccagt ttgttaatat atatgtttac acttacaaga ggatattcgt     660
aatacttta gacgacaaga gacttaggtc aaaaatggac gctggtaaac agcctagact     720
tggtcactga taaatagata attgttagta taatatagta ggatctacaa tgacattaaa     780
attagagcta ttaattaagt tactaataaa taagagaggt tagtaaacag aaagcaggta    840
aaaacaagag cttgctgctg tgtgtttagt tgttgtgagc tcatttctttt aaaagtaatg    900
taaactgatc taaagcacat agaaatttag tacaggttaa aacttttaca agaatttata    960
ttaaacgaaa atcattttat aacatgtctc tcggctgtca ttataatagg gatcacttac   1020
tgatcatcca ttaaaaccctt gttaaaacaa attcaatgag ataaaatatc ttacaatgaa   1080
aagaaggaca atgtctcttt gaaaaaacaa ataggtactc cctccgtccc tctgaaatgt   1140
atacatatgg attggacacg gagactaaga aaaatgtata agtaatgta gagtaaaaag    1200
aaagagaaag aaaagtgggt aaagtagcgg gacccaccaa tatataattg atagatttag    1260
aaaagtagtt gaaagtagtg ggtgggtggg atttttatat tataaaaatt tactattttg    1320
agaaagtttt gaaatgtata gaattgagtg ggacatccat aaaaggaaag tgtatagaat    1380
taaatgggac agagggagta atacctttat gatatataaa ttttttgttat tttgatttca    1440
taagattata aatctatgtt ataatgataa tataatttta aaaataatac tatattaatt    1500
ctgattagtc gattaccgcc ttttataatt ttacaatact gagtaatatg aataaatcag    1560
ttatctgaaa agcaaataat atctttgtaa aacagcgttc ggtcaaatgg gaagttcatg    1620
tgtattcaat agtttttaata taaaagtaaa ttttaaatta attgttattt ttgtttcaga    1680
aatttaaaat aaattattga gcatgggaag ttcacgggca tcattgagca gcactagact    1740
gtttgaacaa tgtatgtccg gtgtacatct atgacctttc aactcaaact agtgaataat    1800
gcattctaga atacatcttt tcaaatttca acaaacacag ctttaacttt tctttcaacg    1860
gattggaatc cttttctaaa cttttttaaaa taaaaaaaat gcattattgt aatatttatc    1920
aacacctcaa cattgatgtt agcgtactat aaataggtgc tcttggtgct ctactatcat    1980
cacatcaatc ttacaccaca aaccttgagc ttaattttttc tacttattct cagcaataac    2040
attctaaata tc                                                        2052
```

<210> SEQ ID NO 2
<211> LENGTH: 851
<212> TYPE: DNA
<213> ORGANISM: Daucus carota -continued

<400> SEQUENCE: 2

| | | | | |
|---|---|---|---|---|
| ctgaaaagga | agttcatcga | tctatcagca | aaattagaga | acttgtgagg tcacagaagt | 60 |
| ctgaaggact | agcggaacct | gaaactgggt | ctcagaagag | gatcacctac gagcaagtga | 120 |
| agaaaatggc | aactttattt | gatgacttgt | tgatatttat | tgagaattac aactttgcag | 180 |
| aaaagccaac | tctgcggttt | caggttctgg | aattaattaa | gcttttacat cactatggaa | 240 |
| gtgatactat | tcgaagcgga | gtggaggaag | aacttgagta | cgtgaatgag aaaaattcag | 300 |
| caacacagta | caagaaagct | ctggaagtaa | tgttgagagt | atgcaataag gagaatacgg | 360 |
| ggatacgtca | aagtattttt | tacgacacaa | tagaaaaggc | agaaagggat aaagtgctct | 420 |
| atgaatggtg | aggaattggg | acggtttagg | ttagcttaaa | aaagtgact tcttacttga | 480 |
| agtaatgaag | tggagtagaa | ctgataagta | aagtaataat | tataagttat taaagtgttt | 540 |
| ggaaaagaaa | tagaagttgt | aaagaaaagt | tagcattttc | tacttccaac ttatttctca | 600 |
| cgacttctta | aaagtacttc | ttactttttt | acacaaacgg | gtcaaggaaa gtggaagcaa | 660 |
| aaagctggag | ttacttctta | taagaatgtt | tatactaaat | gagaaatgac aaacacagaa | 720 |
| atgagaatga | atatgattat | tggtttaata | atagtgtatt | ttatttaaaa agatcgcata | 780 |
| cattaccagc | cagatgaagt | tattcatcac | aactcacaac | aaagtacaaa gaaaagttg | 840 |
| caattctgtc | a | | | | 851 |

<210> SEQ ID NO 3
<211> LENGTH: 2048
<212> TYPE: DNA
<213> ORGANISM: Daucus carota

<400> SEQUENCE: 3

| | | | | |
|---|---|---|---|---|
| catgtgtgcc | ctacagcaca | tagggcctgt | ttggttgaga | gaagcagaag ctgcttctga | 60 |
| cttcttcttc | ttttgacctg | tttgtataaa | gaagtagaaa | tatttttaaa aagctgcgaa | 120 |
| tactaacttc | tctctcacaa | cttccgcttc | ttttccaaac | actttattaa cttttttact | 180 |
| tctcatttct | actccacttc | tttgctataa | gcaagaaatc | acttctttta agctaaccca | 240 |
| aacggcctca | ataaaagatc | attcataaat | gtatctttca | attttaggat aacaatacgt | 300 |
| gaacaggggtt | attttttaac | gtgtcaacaa | attctaataa | ttttacctgg ccggtgaaca | 360 |
| ccgtcttcca | agataatata | ttttaatttt | gtagcctccc | ttttaaccaa attcgcatgc | 420 |
| aggacgactt | aggtgaatac | acattgtact | gtgagtcttt | aaacaaagaa caagtggttc | 480 |
| atgctcagcc | atcaaaattg | acaaaacccg | acacaacact | ctatccacgt actatacttt | 540 |
| tggccgaatg | cttctcaaaa | tgttttttat | atgtaaaata | atgcccatcc aaggataagt | 600 |
| aaaattcccg | tttaaccagt | tgttaatat | atatgtttac | acttacaaga ggatattcgt | 660 |
| aatactttta | gacgacaaga | gacttaggtc | aaaaatggac | gctggtaaac agcctagact | 720 |
| tggtcactga | taaatagata | attgttagta | taatatagta | ggatctacaa tgacattaaa | 780 |
| attagagcta | ttaattaagt | tactaataaa | taagagaggt | tagtaaacag aaagcaggta | 840 |
| aaaacaagag | cttgctgctg | tgtgtttagt | tgttgtgcat | ttctttaaaa gtaatgtaaa | 900 |
| ctgatctaaa | gcacatagaa | atttagtaca | ggttaaaact | tttacaagaa tttatattaa | 960 |
| acgaaaatca | ttttataaca | tgtctctcgg | ctgtcattat | aatagggatc acttactgat | 1020 |
| catccattaa | aacctgtta | aaacaaattc | aatgagataa | aatatcttac aatgaaagaa | 1080 |
| aggacaatgt | ctctttgaaa | aaacaaatag | gtactccctc | cgtccctctg aaatgtatac | 1140 |

```
atatggattg gacacggaga ctaagaaaaa tgtataaagt aatgtagagt aaaaagaaag    1200
agaaagaaaa gtgggtaaag tagcgggacc caccaatata taattgatag atttagaaaa    1260
gtagttgaaa gtagtgggtg ggtgggattt ttatattata aaatttact attttgagaa     1320 agttttgaaa tgtatagaat tgagtgggac atccataaaa ggaaagtgta tagaattaaa    1380
tgggacagag ggagtaatac ctttatgata tataaatttt tgttattttg atttcataag    1440
attataaatc tatgttataa tgataatata attttaaaaa taatactata ttaattctga    1500
ttagtcgatt accgcctttt ataattttac aatactgagt aatatgaata atcagttat     1560 ctgaaaagca aataatatct tgtaaaaca gcgttcggtc aaatgggaag ttcatgtgta     1620
ttcaatagtt ttaatataaa agtaaatttt aaattaattg ttattttgt ttcagaaatt     1680 taaaataaat tattgagcat gggaagttca cgggcatcat tgagcagcac tagactgttt    1740
gaacaatgta tgtccggtgt acatctatga cctttcaact caaactagtg aataatgcat    1800
tctagaatac atcttttcaa atttcaacaa acacagcttt aacttttctt tcaacggatt    1860
ggaatccttt tctaaacttt ttaaaataaa aaaaatgcat tattgtaata tttatcaaca    1920
cctcaacatt gatgttagcg tactataaat aggtgctctt ggtgctctac tatcatcaca    1980
tcaatcttac accacaaacc ttgagcttaa tttttctact tattctcagc aatcacattc    2040
taaagatc                                                            2048

<210> SEQ ID NO 4
<211> LENGTH: 2048
<212> TYPE: DNA
<213> ORGANISM: Daucus carota

<400> SEQUENCE: 4
catgtgtgcc ctacagcaca tagggcctgt ttggttgaga gaagcagaag ctgcttctga     60
cttcttcttc ttttgacctg tttgtataaa gaagtagaaa tattttttaaa aagctgcgaa    120 tactaacttc tctctcacaa cttccgcttc ttttccaaac actttattaa cttttttact    180
tctcatttct actccacttc tttgctataa gcaagaaatc acttctttta agctaaccca    240
aacggcctca ataaagatc attcataaat gtatctttca attttaggat aacaatacgt     300 gaacaggggtt attttttaac gtgtcaacaa attctaataa ttttacctgg ccggtgaaca   360
ccgtcttcca agataatata ttttaattttt gtagcctccc ttttaaccaa attcgcagga   420
cgacttaggt gaatacacat tgtactgtga gtctttaaac aaagaacaag tggttcatgc    480
tcagccatca aaattgacaa aacccgacac aacactctat ccacgtacta tacttttggc    540
cgaatgcttc tcaaaatgtt ttttatatgt aaaataatgc ccatccaagg ataagtaaaa    600 ttcccgtta accagtttgt taatatatat gtttacactt acaagaggat attcgtaata    660
cttttagacg acaagagact taggtcaaaa atggacgctg gtaaacagcc tagacttggt    720
cactgataaa tagataattg ttagtataat atagtaggat ctacaatgac attaaaatta    780
gagctattaa ttaagttact aataaataag agaggttagt aaacagaaag caggtaaaaa    840
caagagcttg ctgctgtgtg tttagttgtt gtgagctcat ttctttaaaa gtaatgtaaa    900
ctgatctaaa gcacatagaa atttagtaca ggttaaaact tttacaagaa tttatattaa    960
acgaaaatca ttttataaca tgtctctcgg ctgtcattat aatagggatc acttactgat    1020
catccattaa aaccttgtta aaacaaattc aatgagataa aatatcttac aatgaaaaga   1080
aggacaatgt ctcttgaaa aaacaaatag gtactccctc cgtccctctg aaatgtatac     1140
atatggattg gacacggaga ctaagaaaaa tgtataaagt aatgtagagt aaaaagaaag    1200
```

-continued

```
agaaagaaaa gtgggtaaag tagcgggacc caccaatata taattgatag atttagaaaa   1260
gtagttgaaa gtagtgggtg ggtgggattt ttatattata aaaatttact attttgagaa   1320
agttttgaaa tgtatagaat tgagtgggac atccataaaa ggaaagtgta tagaattaaa   1380
tgggacagag ggagtaatac ctttatgata tataaatttt tgttattttg atttcataag   1440
attataaatc tatgttataa tgataatata attttaaaaa taatactata ttaattctga   1500
ttagtcgatt accgcctttt ataattttac aatactgagt aatatgaata atcagttat    1560
ctgaaaagca ataatatct  ttgtaaaaca gcgttcggtc aaatgggaag ttcatgtgta   1620
ttcaatagtt ttaatataaa agtaaatttt aaattaattg ttattttgt  ttcagaaatt   1680
taaaataaat tattgagcat gggaagttca cgggcatcat tgagcagcac tagactgttt   1740
gaacaatgta tgtccggtgt acatctatga cctttcaact caaactagtg aataatgcat   1800
tctagaatac atcttttcaa atttcaacaa acacagcttt aacttttctt tcaacggatt   1860
ggaatccttt tctaaacttt ttaaaataaa aaaaatgcat tattgtaata tttatcaaca   1920
cctcaacatt gatgttagcg tactataaat aggtgctctt ggtgctctac tatcatcaca   1980
tcaatcttac accacaaacc ttgagcttaa tttttctact tattctcagc aatcacattc   2040
taaagatc                                                            2048
```

<210> SEQ ID NO 5
<211> LENGTH: 2056
<212> TYPE: DNA
<213> ORGANISM: Daucus carota

<400> SEQUENCE: 5

```
catgtgtgcc ctacagcaca tagggcctgt ttggttgaga gaagcagaag ctgcttctga     60
cttcttcttc ttttgacctg tttgtataaa gaagtagaaa tatttttaaa aagctgcgaa    120
tactaacttc tctctcacaa cttccgcttc ttttccaaac actttattaa cttttttact    180
tctcatttct actccacttc tttgctataa gcaagaaatc acttctttta agctaaccca    240
aacggcctca ataaaagatc attcataaat gtatctttca attttaggat aacaatacgt    300
gaacagggtt attttttaac gtgtcaacaa attctaataa ttttacctgg ccggtgaaca    360
ccgtcttcca agataatata ttttaatttt gtagcctccc ttttaaccaa attcgcatgc    420
aggacgactt aggtgaatac acattgtact gtgagtcttt aaacaaagaa caagtggttc    480
atgctcagcc atcaaaattg acaaaacccg acacaacact ctatccacgt actatacttt    540
tggccgaatg cttctcaaaa tgttttttat atgtaaaata atgcccatcc aaggataagt    600
aaaattcccg tttaaccagt ttgttaatat atatgtttac acttacaaga ggatattcgt    660
aatactttta gacgacaaga gacttaggtc aaaaatggac gctggtaaac agcctagact    720
tggtcactga taaatagata attgttagta taatatagta ggatctacaa tgacattaaa    780
attagagcta ttaattaagt tactaataaa taagagaggt tagtaaacag aaagcaggta    840
aaaacaagag cttgctgctg tgtgtttagt tgttgtgagc tcatttcttt aaaagtaatg    900
taaactgatc taaagcacat agaaatttag tacaggttaa aactttttaca agaatttata    960
ttaaacgaaa atcattttat aacatgtctc tcggctgtca ttataatagg gatcacttac   1020
tgatcatcca ttaaaacctt gttaaaacaa attcaatgag ataaaatatc ttacaatgaa   1080
agaaggaca  atgtctcttt gaaaaaacaa ataggtactc cctccgtccc tctgaaatgt   1140
atacatatgg attggacacg gagactaaga aaaatgtata agtaatgta  gagtaaaaag   1200
```

-continued

```
aaagagaaag aaaagtgggt aaagtagcgg gacccaccaa tatataattg atagatttag    1260
aaaagtagtt gaaagtagtg ggtgggtggg attttatat tataaaaatt tactattttg    1320
agaaagtttt gaaatgtata gaattgagtg ggacatccat aaaaggaaag tgtatagaat    1380
taaatgggac agagggagta ataccttat gatatataaa ttttgttat tttgatttca    1440 taagattata aatctatgtt ataatgataa tataatttta aaaataatac tatattaatt    1500
ctgattagtc gattaccgcc ttttataatt ttacaatact gagtaatatg aataaatcag    1560
ttatctgaaa agcaaataat atctttgtaa aacagcgttc ggtcaaatgg gaagttcatg    1620
tgtattcaat agttttaata taaaagtaaa ttttaaatta attgttattt ttgttcaga    1680 aatttaaaat aaattattga gcatgggaag ttcacgggca tcattgagca gcactagact    1740
gtttgaacaa tgtatgtccg gtgtacatct atgacctttc aactcaaact agtgaataat    1800
gcattctagc tagaatacat cttttcaaat ttcaacaaac acagctttaa cttttctttc    1860
aacggattgg aatccttttc taaacttttt aaaataaaaa aaatgcatta ttgtaatatt    1920
tatcaacacc tcaacattga tgttagcgta ctataaatag gtgctcttgg tgctctacta    1980
tcatcacatc aatcttacac cacaaacctt gagcttaatt tttctactta ttctcagcaa    2040
tcacattcta aagatc                                                   2056

<210> SEQ ID NO 6
<211> LENGTH: 739
<212> TYPE: DNA
<213> ORGANISM: Daucus carota
<220> FEATURE:
<221> NAME/KEY: CDS
<222> LOCATION: (14)..(475)

<400> SEQUENCE: 6
cattctaaat atc atg ggt gcc cag agc cat tca ctc gag atc act tct         49
            Met Gly Ala Gln Ser His Ser Leu Glu Ile Thr Ser
              1               5                  10 tca gtc tcc gca gag aaa ata ttc agc ggc att gtc ctt gat gtt gat        97
Ser Val Ser Ala Glu Lys Ile Phe Ser Gly Ile Val Leu Asp Val Asp
         15                  20                  25 aca gtt att ccc aag gct gcc ccc gga gct tac aag agt gtc gat gtt       145
Thr Val Ile Pro Lys Ala Ala Pro Gly Ala Tyr Lys Ser Val Asp Val
     30                  35                  40 aaa gga gac ggt gga gct gga acc gtc aga att atc acc ctt ccc gaa       193
Lys Gly Asp Gly Gly Ala Gly Thr Val Arg Ile Ile Thr Leu Pro Glu
 45                  50                  55                  60 ggt agc cca atc acc tca atg acg gtt agg act gat gca gtg aac aag       241
Gly Ser Pro Ile Thr Ser Met Thr Val Arg Thr Asp Ala Val Asn Lys
                 65                  70                  75 gag gcc ttg aca tac gat tcc aca gtc att gat gga gac atc ctt cta       289
Glu Ala Leu Thr Tyr Asp Ser Thr Val Ile Asp Gly Asp Ile Leu Leu
             80                  85                  90 gaa ttc atc gaa tcc att gaa acc cat atg gta gtt gtg cca act gct       337
Glu Phe Ile Glu Ser Ile Glu Thr His Met Val Val Val Pro Thr Ala
         95                 100                 105 gac gga ggt agc att acc aag acc act gcc ata ttc cac acc aaa ggc       385
Asp Gly Gly Ser Ile Thr Lys Thr Thr Ala Ile Phe His Thr Lys Gly
    110                 115                 120 gat gcc gtg gtt cct gag gag aac atc aag ttt gca gat gct cag aac       433
Asp Ala Val Val Pro Glu Glu Asn Ile Lys Phe Ala Asp Ala Gln Asn
125                 130                 135                 140 act gct ctt ttc aag gct att gag gcc tac ctc att gct aat              475
Thr Ala Leu Phe Lys Ala Ile Glu Ala Tyr Leu Ile Ala Asn
                145                 150                 155
```

-continued

```
                    145                  150
taagctgagc tctcaacttc cgtaattttta tgagtgagtg gaggaattgc aacgttttct       535
tttgtgtttt gttttcgagc aacttcataa tttacagagt gagtgacagt cagtgacaga       595
attgcaactt tctctttgta ctttgttgtg acttgtgatg aataacttca tctggctggt       655
aatgtatgcg atcttttttaa ataatatgca ctattattaa accaataatc atattcattc      715
tcaaaaaaaa aaaaaaaaaa aaaa                                              739
```

<210> SEQ ID NO 7
<211> LENGTH: 2052
<212> TYPE: DNA
<213> ORGANISM: Daucus carota

<400> SEQUENCE: 7

```
catgtgtgcc ctacagcaca tagggcctgt ttggttgaga gaagcagaag ctgcttctga        60
cttcttcttc ttttgacctg tttgtataaa gaagtagaaa tatttttaaa aagctgcgaa       120
tactaacttc tctctcacaa cttccgcttc ttttccaaac actttattaa cttttttact       180
tctcatttct actccacttc tttgctataa gcaagaaatc acttctttta agctaaccca       240
aacggcctca ataaaagatc attcataaat gtatctttca attttaggat aacaatacgt       300
gaacagggtt attttttaac gtgtcaacaa attctaataa ttttacctgg ccggtgaaca       360
ccgtcttcca agataatata ttttaatttt gtagcctccc ttttaaccaa attcgcatgc       420
aggacgactt aggtgaatac acattgtact gtgagtcttt aaacaaagaa caagtggttc       480
atgctcagcc atcaaaattg acaaaacccg acacaacact ctatccacgt actatacttt       540
tggccgaatg cttctcaaaa tgttttttat atgtaaaata atgcccatcc aaggataagt       600
aaaattcccg tttaaccagt tgttaatat atatgtttac acttacaaga ggatattcgt        660
aatactttta gacgcaaaga gacttaggtc aaaaatggac gctggtaaac agcctagact       720
tggtcactga taaatagata attgttagta taatatagta ggatctacaa tgacattaaa       780
attagagcta ttaattaagt tactaataaa taagagaggt tagtaaacag aaagcaggta       840 aaacaagag cttgctgctg tgtgtttagt tgttgtgagc tcatttcttt aaaagtaatg        900
taaactgatc taaagcacat agaaattag tacaggttaa aacttttaca agaatttata       960
ttaaacgaaa atcattttat aacatgtctc tcggctgtca ttataatagg gatcacttac      1020
tgatcatcca ttaaaaccctt gttaaaacaa attcaatgag ataaaatatc ttacaatgaa    1080
aagaaggaca atgtctcttt gaaaaaacaa ataggtactc cctccgtccc tctgaaatgt     1140
atacatatgg attggacacg gagactaaga aaaatgtata aagtaatgta gagtaaaaag     1200
aaagagaaag aaaagtgggt aaagtagcgg gacccaccaa tatataattg atagatttag    1260 aaagtagtt gaaagtagtg ggtgggtggg attttttatat tataaaaatt tactattttg    1320
agaaagtttt gaaatgtata gaattgagtg ggacatccat aaaaggaaag tgtatagaat    1380
taaatgggac agagggagta ataccttttat gatatataaa tttttgttat tttgatttca    1440
taagattata aatctatgtt ataatgataa tataattttta aaaataatac tatattaatt   1500
ctgattagtc gattaccgcc ttttataatt ttacaatact gagtaatatg aataaatcag    1560
ttatctgaaa agcaaataat atctttgtaa aacagcgttc ggtcaaatgg gaagttcatg   1620
tgtattcaat agttttaata taaaagtaaa ttttaaatta attgttattt tgtttcaga     1680 aatttaaaat aaattattga gcatgggaag ttcacgggca tcattgagca gcactagact   1740
gtttgaacaa tgtatgtccg gtgtacatct atgacctttc aactcaaact agtgaataat   1800
```

```
gcattctaga atacatctttt tcaaatttca acaaacacag ctttaacttt tctttcaacg    1860
gattggaatc cttttctaaa cttttaaaa taaaaaaaat gcattattgt aatatttatc     1920
aacacctcaa cattgatgtt agcgtactat aaataggtgc tcttggtgct ctactatcat   1980
cacatcaatc ttacaccaca aaccttgagc ttaattttc tacttattct cagcaatcac    2040
attctaaaga tc                                                         2052
```

```
<210> SEQ ID NO 8
<211> LENGTH: 154
<212> TYPE: PRT
<213> ORGANISM: Daucus carota

<400> SEQUENCE: 8
```

Met Gly Ala Gln Ser His Ser Leu Glu Ile Thr Ser Ser Val Ser Ala
 1               5                  10                  15

Glu Lys Ile Phe Ser Gly Ile Val Leu Asp Val Asp Thr Val Ile Pro
             20                  25                  30

Lys Ala Ala Pro Gly Ala Tyr Lys Ser Val Asp Val Lys Gly Asp Gly
         35                  40                  45

Gly Ala Gly Thr Val Arg Ile Ile Thr Leu Pro Glu Gly Ser Pro Ile
     50                  55                  60

Thr Ser Met Thr Val Arg Thr Asp Ala Val Asn Lys Glu Ala Leu Thr
 65                  70                  75                  80

Tyr Asp Ser Thr Val Ile Asp Gly Asp Ile Leu Leu Glu Phe Ile Glu
                 85                  90                  95

Ser Ile Glu Thr His Met Val Val Pro Thr Ala Asp Gly Gly Ser
            100                 105                 110

Ile Thr Lys Thr Thr Ala Ile Phe His Thr Lys Gly Asp Ala Val Val
        115                 120                 125

Pro Glu Glu Asn Ile Lys Phe Ala Asp Ala Gln Asn Thr Ala Leu Phe
    130                 135                 140

Lys Ala Ile Glu Ala Tyr Leu Ile Ala Asn
145                 150

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
gggtttcaat ggattcgatg                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
gcagatgctc agaacactgc                                                   20

<210> SEQ ID NO 11
<211> LENGTH: 29
<212> TYPE: DNA
```

<213> ORGANISM: Artificial Sequence
<220> FEATURE:
<223> OTHER INFORMATION: Description of Artificial Sequence: synthetic
      oligonucleotide

<400> SEQUENCE: 11
ggcagctggc acccatgata tttagaatg                              29

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 12
ggcagctgtt cataatttac agagtgagtg acagtcag                    38

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 13
aacaatttca cacaggaaac agctatgacc                             30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 14
cagtcacgac gttgtaaaac gacggccagt                             30

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
ggaagcttca tgtgtgccct acagcaca                               28

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
ggtctagaga tctttagaat gtgattgctg                             30

<210> SEQ ID NO 17
<211> LENGTH: 30
<212> TYPE: DNA
<213> ORGANISM: Artificial Sequence

```
<220> FEATURE:
<223> OTHER INFORMATION: Description of Artificial Sequence: synthetic
      oligonucleotide

<400> SEQUENCE: 17
atcaacacct caacattgat gttagcgtac                                    30

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 18
tctgcatcgg cgaactgatc                                               20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 19
acatgtggag tgaagagtat c                                             21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
gataatcatc gcaagaccgg                                               20

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
gggaattctc agattgtcgt ttcccgcctt cag                                33

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
cagatctggg gaaccctgtg gttg                                          24

<210> SEQ ID NO 23
<211> LENGTH: 30
<212> TYPE: DNA
<213> ORGANISM: Artificial Sequence
<220> FEATURE:
```

```
<223> OTHER INFORMATION: Description of Artificial Sequence: synthetic
      oligonucleotide

<400> SEQUENCE: 23
ggtctagaga tctttagaat gtgattgctg                                    30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 24
aacaatgtat gtccggtgta catctatgac                                    30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 25
ttcataattt acagagtgag tgacagtcag                                    30

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 26
gggaattcct gaaaaggaag ttcatcgatc tatc                               34

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 27
gtaaaacgac ggccagt                                                  17

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 28
aggacgactt aggtgaatac                                               20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: synthetic
```

-continued

```
              oligonucleotide

<400> SEQUENCE: 29
atacatcttt tcaaatttca                                              20
```

PLANT PROMOTERS AND PLANT TERMINATORS

This application is the national phase of international application PCT/JP99/05303 filed Sep. 28, 1999 which designated the U.S. and which was published under PCT Article 21(2) in English on Apr. 13, 2000. The International Application claims priority to Japanese application 10/281, 124, filed on Feb. 10, 1998.

BACKGROUND OF THE INVENTION

1. Field of the Invention

The present invention relates to plant promoters, plant terminators, and the like.

2. Description of the Related Art

There have been many attempts to produce various transgenic plants provided with useful traits by introducing a gene into plants and expressing it, and some of such transgenic plants have already become commercially practical. In order to produce such transgenic plants, it is important to efficiently express a gene introduced into plant cells. A promoter is a major factor that determines transcription level of a gene, and it is generally possible to enhance expression of a gene of interest by placing said gene under the control of a promoter having high transcriptional activity. Furthermore, since a terminator has important effects on processing and degradation of RNA strands generated by transcription, in addition to its function of giving instructions to terminate transcription, it is often effective at increasing expression of a gene of interest to insert a terminator immediately after 3'-end of the translated region of said gene.

However, plant promoters and plant terminators hitherto produced, which may be used in plant breeding by introduction of a gene of interest, are far from enough, and therefore, it is strongly desired to develop new promoters and terminators capable of efficiently expressing a gene of interest in plants.

SUMMARY OF THE INVENTION

Under such circumstances, the present inventors concentrated their efforts on studying promoters and terminators capable of functioning in plant cells, and thereby have found that a gene of interest can be efficiently expressed in plant tissues such as leaves, roots, stems, or the like, by using a DNA having a particular nucleotide sequence. The present invention has been completed on the basis of this finding.

Thus, the present invention provides the following:

1. a promoter comprising the following DNA (a) or (b), characterized in that it is capable of functioning in plant cells:

(a) DNA comprising the nucleotide sequence shown in SEQ ID No: 1 or SEQ ID No: 7, or (b) DNA comprising a nucleotide sequence in which one or more bases are deleted, substituted, or added in the nucleotide sequence shown in SEQ ID No: 1 or SEQ ID No: 7, and which has more than 90% identity to the nucleotide sequence of any region consisting of 250 bp or more within the nucleotide sequence shown in SEQ ID No: 1 or SEQ ID No: 7, wherein said DNA has biological functions equivalent to those of the above DNA (a).

2. a terminator comprising the following DNA (a) or (b), characterized in that it is capable of functioning in plant cells:

(a) DNA comprising the nucleotide sequence shown in SEQ ID No: 2, or (b) DNA comprising a nucleotide sequence in which one or more bases are deleted, substituted, or added in the nucleotide sequence shown in SEQ ID No: 2 and which has more than 90% identity to the nucleotide sequence of any region consisting of 250 bp or more within the nucleotide sequence shown in SEQ ID No: 2, wherein said DNA has biological functions equivalent to those of the above DNA (a).

3. a chimeric gene characterized in that it comprises a promoter of the above 1 and a desired gene linked to each other in the form capable of functioning.

4. a chimeric gene characterized in that it comprises a promoter of the above 1, a desired gene, and a terminator of the above 2 linked to each other in the form capable of functioning.

5. a vector characterized in that it contains a promoter of the above 1.

6. a vector characterized in that it contains a promoter of the above 1 and a desired gene.

7. a vector characterized in that it contains a promoter of the above 1, a desired gene, and a terminator of the above 2.

8. a method of producing a transformant, characterized in that it comprises a step in which any one of a promoter of the above 1, a chimeric gene of the above 3 or 4, and a vector of the above 5, 6 or 7 is introduced into a host cell.

9. a transformant characterized in that it carries any one of a promoter of the above 1, a chimeric gene of the above 3 or 4, and a vector of the above 5, 6 or 7, introduced into the host cell.

10. a transformant of the above 9 characterized in that the host cell is a microbial cell or a plant cell.

11. a method of expressing a gene, characterized in that it comprises a step in which a promoter of the above 1 and a desired gene located downstream from said promoter are placed in a host cell, and a step in which the desired gene is expressed in the host cell under the control of said promoter.

12. a method of expressing a gene, characterized in that it comprises a step in which a terminator of the above 2 and a desired gene located upstream from said terminator are placed in a host cell, and a step in which the desired gene is expressed in the host cell under the control of said terminator.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE INVENTION

Figure 1:
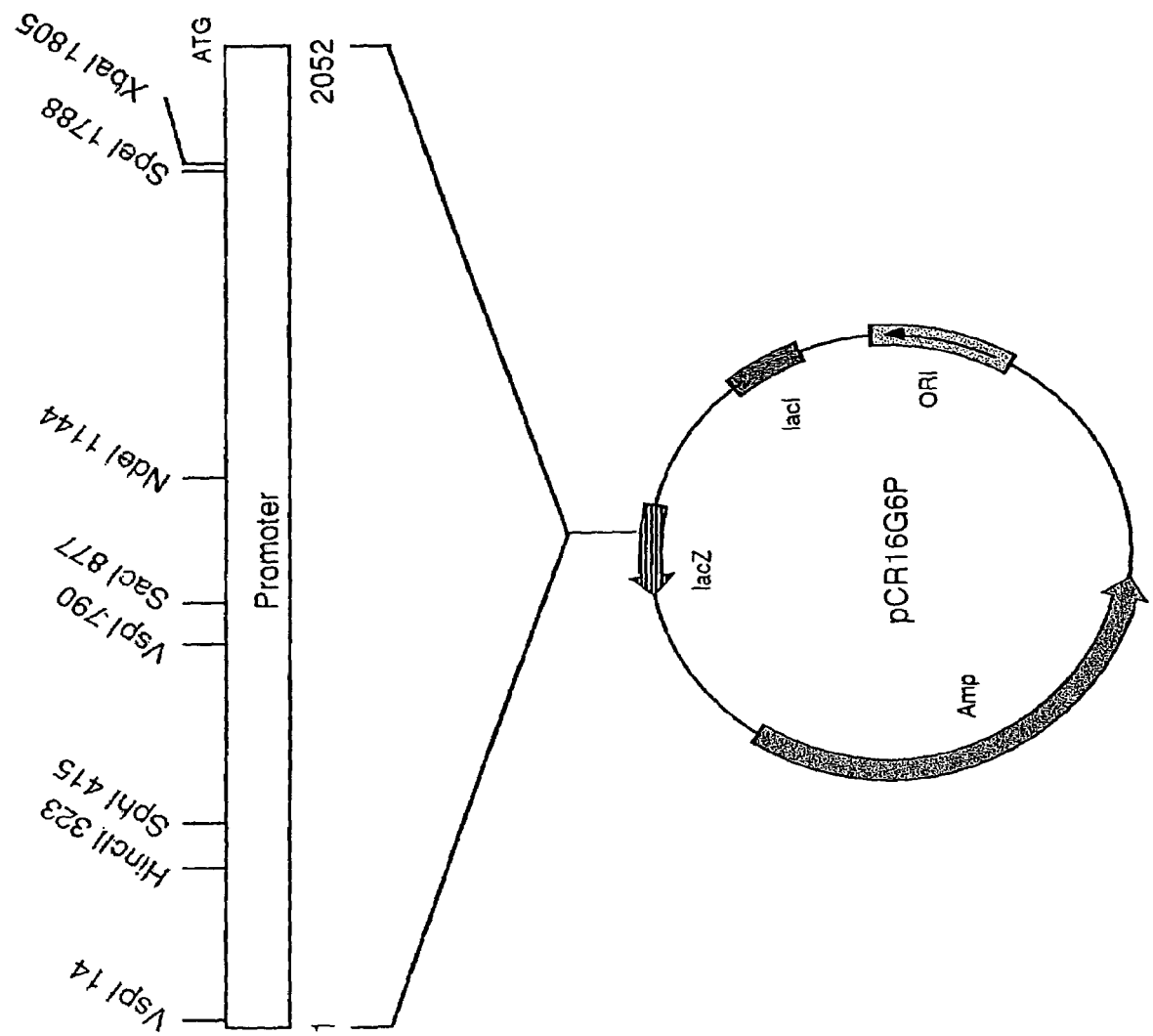
FIG. 1 shows the restriction enzyme map of plasmid pCR16G6P containing a promoter of the present invention. "Promoter" indicates the promoter of the present invention. Likewise, "Amp" represents ampicillin resistance gene; "lac I" represents the repressor protein gene of the lactose operon; "lac Z" represents β-galactosidase gene; and "ORI" represents an origin of replication.
Figure 2:
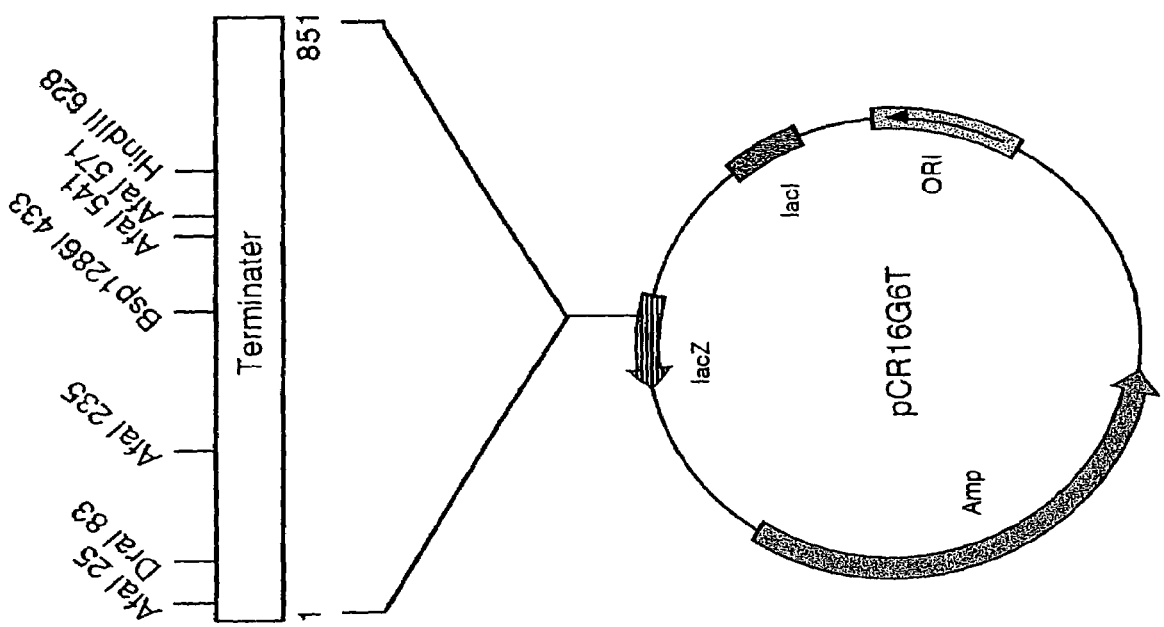
FIG. 2 shows the restriction enzyme map of plasmid pCR16G6T containing a terminator of the present invention. "Terminator" indicates the terminator of the present invention. Likewise, "Amp" represents ampicillin resistance gene; "lac I" represents the repressor protein gene of the lactose operon; "lac Z" represents β-galactosidase gene; and "ORI" represents an origin of replication.

The present invention is described below in more detail.

The genetic engineering techniques used in the present invention may be conducted according to the usual procedures, for example, described in J. Sambrook, E. F., Frisch, and T. Maniatis, "Molecular Cloning 2nd edition" (Cold Spring Harbor Laboratory Press, 1989); and D. M. Glover, "DNA Cloning" (IRL Press, 1985).

In the present invention, the term "promoter" means DNA that has a function of initiating transcription of a gene of interest located downstream from said DNA.

A promoter of the present invention comprises the following DNA (a) or (b) (hereinafter referred to as the present promoter DNA):

(a) DNA comprising the nucleotide sequence shown in SEQ ID No: 1 or SEQ ID No: 7, or (b) DNA comprising a nucleotide sequence in which one or more bases are deleted, substituted, or added in the nucleotide sequence shown in SEQ ID No: 1 or SEQ ID No: 7, and which has more than 90% identity to the nucleotide sequence of any region consisting of 250 bp or more within the nucleotide sequence shown in SEQ ID No: 1 or SEQ ID No: 7, wherein said DNA has biological functions equivalent to those of the above DNA (a).

In this context, examples of "nucleotide sequence in which one or more bases are deleted, substituted, or added" may include those nucleotide sequences that contain naturally occurring variations resulted from the species or individual difference between organisms or the difference between tissues from which the DNAs are obtained, or variations artificially introduced into the DNA. DNA which "has biological functions equivalent to those of the above DNA (a)" may be, for example, those DNAs that comprise a nucleotide sequence in which one or more bases are deleted, substituted, or added in the nucleotide sequence shown in SEQ ID No: 1 or SEQ ID No: 7, provided they retain the promoter functions in plant cells, and that have more than 90% identity to the nucleotide sequence of any region consisting of 250 bp or more within the nucleotide sequence shown in SEQ ID No: 1 or SEQ ID No: 7. Such DNAs may be those DNAs that are cloned from natural sources, or that contain artificially introduced deletion, substitution, or addition of base(s) in DNAs cloned from natural sources, or that are artificially produced by chemical synthesis.

And it is possible to increase expression efficiency of a desired gene by conducting a step in which a promoter of the present invention and the desired gene located downstream from said promoter are placed in host cells, and a step in which the desired gene is expressed in the host cells under the control of said promoter.

The present promoter DNAs may be isolated from, for example, genomic DNA of carrots such as *Daucus carota*, by using a PCR method.

Specifically, tissues are collected from, for example, leaves of carrots such as *Daucus carota*, and tissues obtained are frozen in liquid nitrogen, followed by physical grinding with a mortar or the like into fine powdered tissue pieces. Genomic DNA is extracted from the tissue pieces by the usual method. The extraction process may be conducted, for example, by the CTAB method described in, e.g., M. Shure et al. Cell, 35:225 (1983), or by the urea-phenol method described in, e.g., S. O. Rogers and A. J. Bendich, Plant Mol. Biol., 5:69 (1985). For example, genomic DNA obtained may be used as template to conduct one to several rounds of PCR (reaction conditions: for example, one to several rounds of PCR each conducted for 30–40 cycles of incubation at 94° C. for 1 min; at 55° C. for 2 min; and then at 74° C. for 3 min per cycle) using, as primers, an oligonucleotide having the nucleotide sequence indicated by base numbers 1 to 20 in SEQ ID No: 1 or SEQ ID No: 7, and an oligonucleotide having a nucleotide sequence complementary to the nucleotide sequence indicated by base numbers 2029 to 2052 in SEQ ID No: 1 or SEQ ID No: 7, to amplify DNA comprising the nucleotide sequence shown in SEQ ID No: 1 or SEQ ID No: 7, or DNA comprising a nucleotide sequence in which one or more bases are deleted, substituted, or added in the nucleotide sequence shown in SEQ ID No: 1 or SEQ ID No: 7. Oligonucleotides used as such primers may be designed as appropriate on the basis of the nucleotide sequence shown in SEQ ID No: 1 or SEQ ID No: 7, and may optionally have an additional nucleotide sequence, such as a restriction enzyme-recognition nucleotide sequence, attached to their 5' ends.

A DNA amplified as described above may be cloned into a vector according to the usual methods described in, for example, "Molecular Cloning: A Laboratory Manual 2nd edition" (1989) (Cold Spring Harbor Laboratory Press) or "Current Protocols In Molecular Biology" (1987) (John, Wiley & Sons, Inc., ISBN0-471-50338-X). Specifically, the cloning may be achieved using a plasmid vector such as one included in TA Cloning Kit (Invirogen Co.) or pBluescript II (STRATAGENE). The nucleotide sequence of the cloned DNA may be analyzed, for example, by the dye deoxy terminating method described in, e.g., "Molecular Cloning: A Laboratory Manual 2nd edition" (1989) (Cold Spring Harbor Laboratory Press) 13.42–13.74. To prepare samples for nucleotide sequence analysis, commercially available reagents such as ABI PRISM Dye Terminator Cycle Sequencing Ready Reaction Kit (PE Biosystems) may optionally be used.

A reporter gene, for example, β-glucuronidase gene, is linked downstream to the DNA obtained as described above, cloned as needed into a vector, and then introduced into cultured plant cells such as tobacco cultured cell BY-2 by using procedures such as the particle gun method or *Agrobacterium* infection method as described below. To obtain the present promoter DNA, the presence or absence of the promoter functions of the above DNA may be then confirmed by preparing a cell extract from the cultured cells and measuring the extract for its β-glucuronidase activity by an enzymological technique to use the value of said activity as an indicator, or by immersing the cultured cells in a staining solution containing 5-bromo-4-chloro-3-indolyl-β-D-glucuronide and observing deposition of the blue dye to use the degree of dye deposition as an indicator. Alternatively, the above DNA linked to a reporter gene may also be similarly introduced into a plant cell such as a cell from a wild-type strain of tobacco, and a plant may be regenerated from the cell. To obtain the present promoter DNA, the presence or absence of the promoter functions of the above DNA may be then confirmed by measuring the β-glucuronidase activity in tissues from the plant or its progeny, or by immersing tissues or sections thereof from the plant or its progeny in a staining solution containing 5-bromo-4-chloro-3-indolyl-β-D-glucuronide and observing deposition of the blue dye to use the degree of dye deposition as an indicator. Besides β-glucuronidase gene, other genes such as a luciferase gene, a chloramphenicol acetyltransferase gene, and a green fluorescent protein gene may also be used as a reporter gene.

Furthermore, the present promoter DNA may also be obtained by labeling, for example, DNA comprising at least part of the nucleotide sequence shown in SEQ ID No: 1 or SEQ ID No: 7, and hybridizing it as a probe to DNAs derived from a plant or the like to detect and clone DNAs to which the probe specifically binds.

In this procedure, for example, a genomic DNA library derived from a plant such as carrot may be used as DNAs to which the above probe is allowed to hybridize. As such DNA libraries, commercially available genomic DNA libraries may be used, or genomic DNA libraries may also be prepared for use, according to the usual procedures for library preparation described in, e.g., "Molecular Cloning: A Laboratory Manual 2nd edition" (1989) (Cold Spring Harbor Laboratory Press) or "Current Protocols In Molecular Biology" (1987) (John Wiley & Sons, Inc., ISBN0-471-50338-X), for example, using a λ vector such as λ FIX II, λ EMBL3, λ EMBL4, or λ DASH II (STRATAGENE) together with Gigapack packaging Extracts (STRATAGENE) for in vitro packaging.

The methods by which a probe is allowed to hybridize with such DNAs may include colony hybridization and plaque hybridization, and an appropriate method may be selected depending on the type of vector used in the library preparation. In the case that the library used has been constructed with a plasmid vector, colony hybridization is conducted. Specifically, DNAs in the library are firstly introduced into host microorganisms to obtain transformants, and the transformants obtained were diluted, plated onto agar medium, and cultured at 37° C. until colonies appear. On the other hand, in the case that the library used has been constructed with a phage vector, plaque hybridization is conducted. Specifically, host microorganisms and phages in the library are firstly mixed under conditions that allow infection, then further mixed with soft agar medium, and plated onto agar medium. It is then cultured at 37° C. until plaques appear. More particularly, for example, according to the procedures described in, e.g., "Molecular Cloning 2nd edition" (J. Sambrook, E. F. Frisch, and T. Maniatis, Cold Spring Harbor Laboratory Press, 1989) 2.60–2.65, about $9.0 \times 10^5$ pfu of the phage library is spread in NZY agar medium at a density of 0.1–1.0 pfu per $mm^2$ agar medium, and cultured at 37° C. for 6–10 hours.

In both of the above hybridization procedures, a membrane is then put onto the surface of the agar medium on which the above culture has been grown, and the transformants carrying plasmids or the phages are transferred onto the membrane. After treating with alkali, the membrane is neutralized, and further treated to fix DNAs onto the membrane. More particularly, for example, in the case of plaque hybridization, a membrane such as nitrocellulose or nylon membrane (e.g., Hybond-N+ (Amersham Pharmacia Biotech, Inc.)) is put onto the above-described agar medium, and left for about one minute to allow phage particles to adsorb on the membrane, according to the usual procedures described in, e.g., "Kuroningu to Shikuensu: Shokubutsu Baiotekunoroji Jikken Manyuaru (translation: Cloning and Sequencing: Plant Biotechnology Experimental Manual)" (Watanabe and Sugiura eds., Noson-bunka-sha, 1989). Next, the membrane is immersed in an alkaline solution (1.5 M sodium chloride, 0.5 N NaOH) for about 3 minutes to lyse the phage particles and thereby release phage DNAs onto the membrane, and then treated by immersing the membrane in a neutralizing solution (1.5 M sodium chloride, 0.5 M Tris-HCl buffer, pH 7.5) for about 5 minutes. After washing with a washing solution (300 mM sodium chloride, 30 mM sodium citrate, 200 mM Tris-HCl buffer) for about 5 minutes, the membrane is baked at about 80° C. for about 90 minutes to fix the phage DNAs onto the membrane.

The membrane prepared is used to conduct hybridization with the above DNA as a probe. Hybridization may be conducted as described in, for example, D. M. Glover ed., "DNA cloning, a practical approach" (IRL Press, 1985, ISBN 0-947946-18-7); "Kuroningu to Shikuensu: Shokubutsu Baiotekunoroji Jikken Manyuaru (translation: Cloning and Sequencing: Plant Biotechnology Experimental Manual)" (Watanabe and Sugiura eds., Noson-bunka-sha, 1989); or "Molecular Cloning 2nd edition" (J. Sambrook, E. F. Frisch, and T. Maniatis, Cold Spring Harbor Laboratory Press, 1989).

In order to label the DNA used as a probe with a radioisotope, for example, Random Labeling Kit (Boehringer Mannheim or Takara Shuzo Co., Ltd.) may be used, or it is also possible to label the DNA by conducting PCR using DNA for probe as a template, with substituting [α-$^{32}$P] dCTP for dCTP. Alternatively, in order to label the DNA used as a probe with a fluorescent dye, for example, ECL Direct Nucleic Acid Labeling and Detection System (Amersham Pharmacia Biotech, Inc.) may be used.

Many kinds of reagent and temperature conditions are available for conducting hybridization. For example, a prehybridization solution which contains 450–900 mM sodium chloride, 45–90 mM sodium citrate, 0.1–1.0% sodium dodecyl sulfate (SDS), and 0–200 µg/ml denatured non-specific DNA and which, in some cases, may optionally contain each 0–0.2% albumin, Ficoll, polyvinylpyrrolidone, or the like, preferably a pre-hybridization solution containing 900 mM sodium chloride, 90 mM sodium citrate, 1% SDS, and 100 µg/ml denatured calf-thymus DNA, is prepared in a volume of 50–200 µl per $cm^2$ of the membrane prepared as above, and the above membrane is immersed and incubated in the solution at 42–68° C. for 1–4 hours, preferably at 45° C. for 2 hours. Then, a hybridization solution which contains, for example, 450–900 mM sodium chloride, 45–90 mM sodium citrate, 0.1–1.0% SDS, and 0–200 µg/ml denatured non-specific DNA and which, in some cases, may optionally contain each 0–0.2% albumin, Ficoll, polyvinylpyrrolidone, or the like, preferably a hybridization solution containing 900 mM sodium chloride, 90 mM sodium citrate, 1% SDS, and 100 µg/ml denatured calf-thymus DNA, is mixed with the probe obtained by the above described procedures (at an amount equivalent to $1.0 \times 10^4$–$2.0 \times 10^6$ cpm per $cm^2$ membrane) to prepare a mixed solution in a volume of 50–200 µl per $cm^2$ membrane, and the membrane is immersed and incubated in the mixed solution at 42–68° C. for 4–20 hours, preferably at 45° C. for 16 hours, to achieve hybridization. After the hybridization reaction, the membrane is recovered, and washed 1–4 times each for 10–60 minutes, preferably twice each for 15 minutes, with a washing solution, for example, which contains 15–300 mM sodium chloride, 1.5–30 mM sodium citrate, 0.1–1.0% SDS, and the like, at 42–68° C., preferably with a washing solution containing 300 mM sodium chloride, 30 mM sodium citrate, and 1% SDS at 55° C. Furthermore, the membrane is briefly rinsed with 2×SSC solution (300 mM sodium chloride, 30 mM sodium citrate), and then dried. The positions of DNAs on the membrane that hybridize with the probe used are detected, for example, by subjecting this membrane to autoradiography to detect the positions of the probe on the membrane. The clones corresponding to the positions of the detected DNAs on the membrane are identified on the original agar medium, and can be picked up to isolate clones carrying those DNAs. Specifically, the membrane is exposed to an imaging plate (Fuji Photo Film Co., Ltd.) for 4 hours, and this imaging plate is analyzed using BAS 2000 (Fuji Photo Film Co., Ltd.) to detect signals. From the agar medium used for preparation of the membrane, the parts corresponding to the positions at which signals are detected are cut out as about 5-mm square sections, and these sections are immersed in about 500 µl of SM buffer (50 mM Tris-HCl buffer, pH 7.5, 0.1 M sodium chloride, 7 mM magnesium sulfate, 0.01% gelatin) for 2–16 hours, preferably for 3 hours, to elute the phage particles. The phage particle eluate obtained is spread on agar medium according to the method described in "Molecular Cloning 2nd edition" (J. Sambrook, E. F. Frisch, and T. Maniatis, Cold Spring Harbor Laboratory Press, 1989) 2.60–2.65, and cultured at 37° C. for 6–10 hours. Using this agar medium, phage DNAs are fixed onto a membrane in the same manner as that described above, and this membrane and the above-described probe are used to conduct hybridization. From the sections, of the agar medium used for preparation of the membrane, that correspond to the positions at which signals are detected, phage particles are eluted, spread on agar medium, and used in preparation of membrane in the same manner as that described above, to conduct hybridization. Such identification and purification steps are repeated to obtain a phage clone that carries DNA having a nucleotide sequence which hybridizes to the probe used.

DNA contained in a clone obtained by conducting a screening via hybridization as described above may be subcloned into a plasmid vector which allows easy preparation or analysis of DNA, such as commercially available pUC18, pUC19, pBluescript KS+, or pBluescript KS−, to prepare the plasmid DNA, and its nucleotide sequence can be determined using the dye deoxy terminating method described in, for example, Molecular Cloning: A Laboratory Manual 2nd edition" (1989) (Cold Spring Harbor Laboratory Press) 13.42–13.74. Samples used for nucleotide sequence analysis may be prepared, for example, according to the primer extension method described in, e.g., "Molecular Cloning 2nd edition" (J. Sambrook, E. F. Frisch, and T. Maniatis, Cold Spring Harbor Laboratory Press, 1989) 13.15. Alternatively, in order to analyze the nucleotide sequence, the phage clone may be amplified in NZYM liquid medium according to the method described in, for example, "Molecular Cloning 2nd edition" (J. Sambrook, E. F. Frisch, and T. Maniatis, Cold Spring Harbor Laboratory Press, 1989) 2.60–2.65, to prepare a phage solution. From this phage solution, the phage clone DNA may be then extracted using, for example, Lambda-TRAP PLUS DNA Isolation Kit (Clontech Laboratories, Inc.), and the DNA obtained may be used as a template in the primer extension method described above to prepare samples for nucleotide sequence analysis.

The present promoter DNA may be obtained by assaying, as described above, the promoter functions of DNA thus obtained.

The present promoter DNA may also be obtained by introducing variation(s) into the nucleotide sequence of DNA comprising the nucleotide sequence shown in SEQ ID No: 1 or SEQ ID No: 7. Specifically, variations may be randomly introduced into DNA comprising the nucleotide sequence shown in SEQ ID No: 1 or SEQ ID No: 7, for example, according to the method described in, e.g., A. Greener, and M. Callahan, Strategies, 1994, vol. 7, pp. 32–34, or may be site-specifically introduced into DNA comprising the nucleotide sequence shown in SEQ ID No: 1 or SEQ ID No: 7, for example, according to the gapped duplex method described in, e.g., W. Kramer et al., Nucleic Acids Research, 1984, vol. 12, p. 9441 or W. Kramer and H. J. Frits, Methods in Enzymology, 1987, vol. 154, p. 350, or according to the Kunkel method described in, e.g., T. A. Kunkel, Proc. of Natl. Acad. Sci. U.S.A., 1985, vol. 82, p. 488 or T. A. Kunkel et al., Methods in Enzymology, 1987, vol. 154, p. 367. Alternatively, an oligonucleotide primer having a nucleotide sequence in which one or more bases are deleted, substituted, or added in part of the nucleotide sequence shown in SEQ ID No: 1 or SEQ ID No: 7 may be used as a primer to conduct PCR, in order to amplify DNA comprising a nucleotide sequence in which one or more bases are deleted, substituted, or added in the nucleotide sequence shown in SEQ ID No: 1 or SEQ ID No: 7. Furthermore, a chimeric DNA in which partial nucleotide sequence(s) of one or more segments within the nucleotide sequence shown in SEQ ID No: 1 or SEQ ID No: 7 are replaced with part of nucleotide sequence of other promoter(s) may be produced, and DNA having a nucleotide sequence in which part of the nucleotide sequence shown in SEQ ID No: 1 is deleted may also be prepared, for example, according to the method described in, e.g., S. Henikoff et al., Gene, 1984, vol. 28, p. 351 or C. Yanisch-Perron et al., Gene, 1985, vol. 33, p. 103. The present promoter DNA may be obtained by assaying, as described above, the promoter functions of DNA thus obtained.

Among the present promoter DNAs obtained as described above, a promoter of the present invention may contain either of the above-defined DNA (a) or (b), or both of (a) and (b), and it may also contain these DNAs repeatedly.

In addition, a promoter of the present invention may further contain a nucleotide sequence having an effect of increasing transcription efficiency of a gene in plants. Such nucleotide sequence may be, for example, a nucleotide sequence that constitutively exhibits its increasing effect on transcription efficiency, or a nucleotide sequence that exhibits its increasing effect on transcription efficiency species-, tissue-, or stage-specifically, or a nucleotide sequence of which increasing effect on transcription efficiency is induced, for example, by infection of a pathogenic microorganism, or by stress such as light, heat, drought, salts, or wound. Specific examples of nucleotide sequence having an effect of increasing efficiency in transcribing a gene in plants include, for example, the transcription translation activating nucleotide sequence in which a region of mannopine synthetic enzyme gene from the base at the 318th position through the base at the 138th position upstream from the point of transcription is linked downstream to a region of *Agrobacterium* octopine synthetic enzyme gene from the base at the 333rd position through the base at the 116th position upstream from the point of transcription, and the transcription activating nucleotide sequence in which a region of octopine synthetic enzyme gene from the base at the 333rd position through the base at the 116th position upstream from the point of transcription is linked downstream to a region of mannopine synthetic enzyme gene from the base at the 318th position through the base at the 213th position upstream from the point of transcription (The Plant Journal, 7(4):661–676 (1995)); the nucleotide sequence comprising the bases of cauliflower mosaic virus 35S promoter from the 343rd position through the 91st position upstream from the point of transcription (Nature, 313:810–812 (1985)); the nucleotide sequence comprising the bases of tomato ribulose-1,5-bisphosphate carboxylase/oxygenase small subunit gene (rbc-3A) from the 1099th position through the 205th position upstream from the point of transcription (Plant Cell, 1:217–227 (1990)); the nucleotide sequence comprising the bases of tobacco PR1a gene from the 902nd position through the 287th position upstream from the point of transcription (Plant Cell, 2:357–366 (1990)); and the nucleotide sequence comprising the bases of potato protease inhibitor gene (PI-II) from the 1300th position through the 195th position upstream from the point of transcription (Plant Cell, 2:61–70 (1990)).

Furthermore, a promoter of the present invention may contain a nucleotide sequence having an increasing effect on transcription efficiency that is included in the nucleotide sequence shown in SEQ ID No: 1 or SEQ ID No: 7. It is also possible to identify such nucleotide sequence and to prepare a promoter of the present invention repeatedly containing such nucleotide sequence or to prepare a novel plant promoter by linking such nucleotide sequence to another DNA having promoter functions in plant cells. In order to identify such nucleotide sequence, for example, a reporter gene may be expressed in plant cells under the control of a variety of the present promoter DNAs, and the amounts of expression are compared to analyze the nucleotide sequences contributing to the increasing effect on transcription efficiency. More particularly, for example, various DNAs comprising a nucleotide sequence in which one or more bases are deleted, substituted, or added in the nucleotide sequence shown in SEQ ID No: 1 or SEQ ID No: 7 are prepared, and a reporter gene, for example, β-glucuronidase gene, is linked downstream to each of the DNAs. These constructs are then introduced into cultured plant cells such as tobacco cultured cell BY-2 by using procedures such as the particle gun method or *Agrobacterium* infection as described below. To define nucleotide sequences that contribute to the increasing effect on transcription efficiency, the amount of expression of the reporter gene in each cell may be then compared with each other by preparing a cell extract from the cultured cells and measuring the extract for its β-glucuronidase activity by an enzymological technique to use the value of activity as an indicator, or by immersing the cultured cells in a staining solution containing 5-bromo-4-chloro-3-indolyl-β-D-glucuronide and observing deposition of the blue dye to use the degree of dye deposition as an indicator, and the results may be collated with the nucleotide sequences of the above DNA linked to the reporter gene. Alternatively, the above DNA linked to a reporter gene may also be similarly introduced into a plant cell such as a cell from a wild-type strain of tobacco, and the plant may be regenerated from the cell. To define the nucleotide sequences that contribute to the increasing effect on transcription efficiency, the amount of expression of the reporter gene controlled by each of the above DNAs may be then compared by measuring the β-glucuronidase activity in tissues from the plant or its progeny, or by immersing tissues or sections thereof from the plant or its progeny in a staining solution containing 5-bromo-4-chloro-3-indolyl-β-D-glucuronide and observing deposition of the blue dye to use the degree of dye deposition as an indicator.

In the present invention, the term "terminator" means DNA that has a function of giving instructions to terminate transcription of a gene of interest located upstream from said DNA. A terminator of the present invention comprises the following DNA (a) or (b) (hereinafter referred to as the present terminator DNA):

(a) DNA comprising the nucleotide sequence shown in SEQ ID No: 2, or (b) DNA comprising a nucleotide sequence in which one or more bases are deleted, substituted, or added in the nucleotide sequence shown in SEQ ID No: 2 and which has more than 90% identity to the nucleotide sequence of any region consisting of 250 bp or more within the nucleotide sequence shown in SEQ ID No: 2, wherein said DNA has biological functions equivalent to those of the above DNA (a).

In this context, examples of "nucleotide sequence in which one or more bases are deleted, substituted, or added" may include those nucleotide sequences that contain naturally occurring variations resulted from the species or individual difference between organisms or the difference between tissues from which the DNAs are obtained, or variations artificially introduced into the DNA. DNA which "has biological functions equivalent to those of the above DNA (a)" may be, for example, those DNAs that comprise a nucleotide sequence in which one or more bases are deleted, substituted, or added in the nucleotide sequence shown in SEQ ID No: 2, provided they retain the terminator functions in plant cells. Such DNAs may be those DNAs that are cloned from natural sources, or that contain artificially introduced deletion, substitution, or addition of base(s) in DNAs cloned from natural sources, or that are artificially produced by chemical synthesis.

And it is possible to increase expression efficiency of a desired gene by conducting a step in which a terminator of the present invention and the desired gene located upstream from said terminator are placed in host cells, and a step in which the desired gene is expressed in the host cells under the control of said terminator.

The present terminator DNAs may be isolated according to the methods described above for obtaining the present promoter DNAs based on the nucleotide sequence shown in SEQ ID No. 2. A specific example may be the method in which genomic DNA derived from a plant such as carrot is used as template to conduct one to several rounds of PCR (reaction conditions: for example, one to several rounds of PCR each conducted for 30–40 cycles of incubation at 94° C. for 1 min; at 55° C. for 2 min; and then at 74° C. for 3 min per cycle) using, as primers, an oligonucleotide having the nucleotide sequence indicated by base numbers 1 to 20 in SEQ ID No: 2 and an oligonucleotide having a nucleotide sequence complementary to the nucleotide sequence indicated by base numbers 827 to 851 in SEQ ID No: 2.

In order to confirm the terminator functions of the present terminator DNA in plant cells, for example, a promoter capable of functioning in plant cells, a reporter gene such as β-glucuronidase gene, and the present terminator DNA are linked together in the form that allows expression, while, as a control, the promoter and β-glucuronidase gene are linked in the same manner. Each of these constructs is introduced into cultured plant cells, for example, tobacco cultured cell BY-2, by using procedures such as the particle gun method or *Agrobacterium* infection as described below. Then, by preparing a cell extract from each cell and measuring the extract for its β-glucuronidase activity to use the value of said activity as an indicator, or by immersing said cells in a staining solution containing 5-bromo-4-chloro-3-indolyl-β-D-glucuronide and observing deposition of the blue dye to use the degree of dye deposition as an indicator, it is confirmed that the amount of β-glucuronidase expression is higher, when compared to the control, in plant cells into which the promoter, β-glucuronidase gene, and the present terminator DNA linked together are introduced. Or similarly, a promoter capable of functioning in plant cells, β-glucuronidase gene, and the present terminator DNA are linked together, while, as a control, the promoter and β-glucuronidase gene are linked in the same manner, and each of these constructs are then introduced into a plant cell such as a cell from a wild-type strain of tobacco, and a plant may be regenerated from the cell. The presence or absence of terminator functions of the present terminator DNA may be confirmed by measuring the β-glucuronidase activity in tissues from the plant regenerated or its progeny, or by immersing tissues or sections thereof from the plant or its progeny in a staining solution containing 5-bromo-4-chloro-3-indolyl-β-D-glucuronide and observing deposition of the blue dye to use the degree of dye deposition as an indicator.

Furthermore, the present terminator DNA may also be obtained by labeling, for example, DNA comprising at least part of the nucleotide sequence shown in SEQ ID No: 2, and hybridizing it as a probe to DNAs derived from a plant or the like to detect and clone DNAs to which the probe specifically binds.

In this procedure, for example, a genomic DNA library derived from a plant such as carrot may be used as DNAs to which the above probe is allowed to hybridize. As such DNA libraries, commercially available genomic DNA libraries may be used, or genomic DNA libraries may also be prepared for use, according to the usual procedures for library preparation described in, e.g., "Molecular Cloning: A Laboratory Manual 2nd edition" (1989) (Cold Spring Harbor Laboratory Press) or "Current Protocols In Molecular Biology" (1987) (John Wiley & Sons, Inc., ISBN0-471-50338-X), for example, using a λ vector such as λ FIX II, λ EMBL3, λ EMBL4, or λ DASH II (STRATAGENE) together with Gigapack packaging Extracts (STRATAGENE) for in vitro packaging.

The method by which a probe is allowed to hybridize with such DNAs may include colony hybridization and plaque hybridization, and an appropriate method may be selected depending on the type of vector used in the library preparation. In the case that the library used has been constructed with a plasmid vector, colony hybridization is conducted. Specifically, DNAs in the library are firstly introduced into host microorganisms to obtain transformants, and the transformants obtained were diluted, plated onto agar medium, and cultured at 37° C. until colonies appear. On the other hand, in the case that the library used has been constructed with a phage vector, plaque hybridization is conducted. Specifically, host microorganisms and phages in the library are firstly mixed under conditions that allow infection, then further mixed with soft agar medium, and plated onto agar medium. It is then cultured at 37° C. until plaques appear. More particularly, for example, according to the procedures described in, e.g., "Molecular Cloning 2nd edition" (J. Sambrook, E. F. Frisch, and T. Maniatis, Cold Spring Harbor Laboratory Press, 1989) 2.60–2.65, about $9.0 \times 10^5$ pfu of the phage library is spread in NZY agar medium at a density of 0.1–1.0 pfu per $mm^2$ agar medium, and cultured at 37° C. for 6–10 hours.

In both of the above hybridization procedures, a membrane is then put onto the surface of the agar medium on which the above culture has been grown, and the transformants carrying plasmids or the phages are transferred onto the membrane. After treating with alkali, the membrane is neutralized, and further treated to fix DNAs onto the membrane. More particularly, for example, in the case of plaque hybridization, a filer such as nitrocellulose or nylon membrane (e.g., Hybond-N+ (Amersham Pharmacia Biotech, Inc.)) is put onto the above-described agar medium, and left for about one minute to allow phage particles to adsorb on the membrane, according to the usual procedures described in, e.g., "Kuroningu toShikuensu: Shokubutsu Baiotekunoroji Jikken Manyuaru (translation: Cloning and Sequencing: Plant Biotechnology Experimental Manual)" (Watanabe and Sugiura eds., Noson-bunka-sha, 1989). Next, the membrane is immersed in an alkaline solution (1.5 M sodium chloride, 0.5 N NaOH) for about 3 minutes to lyse the phage particles and thereby release phage DNAs onto the membrane, and then treated by immersing the membrane in a neutralizing solution (1.5 M sodium chloride, 0.5 M Tris-HCl buffer, pH 7.5) for about 5 minutes. After washing with a washing solution (300 mM sodium chloride, 30 mM sodium citrate, 200 mM Tris-HCl buffer) for about 5 minutes, the membrane is baked at about 80° C. for about 90 minutes to fix the phage DNAs onto the membrane.

The membrane thus prepared is used to conduct hybridization with the above DNA as a probe. For hybridization procedures, one may refer to, for example, D. M. Glover ed., "DNA cloning, a practical approach" (IRL Press, 1985, ISBN 0-947946-18-7); "Kuroningu to Shikuensu: Shokubutsu Baiotekunoroji Jikken Manyuaru (translation: Cloning and Sequencing: Plant Biotechnology Experimental Manual)" (Watanabe and Sugiura eds., Noson-bunka-sha, 1989); or "Molecular Cloning 2nd edition" (J. Sambrook, E. F. Frisch, and T. Maniatis, Cold Spring Harbor Laboratory Press, 1989).

In order to label the DNA used as a probe with a radioisotope, for example, Random Labeling Kit (Boehringer Mannheim or Takara Shuzo Co., Ltd.) may be used, or it is also possible to label the DNA by conducting PCR using DNA for probe as a template, with substituting [α-$^{32}$P] dCTP for dCTP used in the usual PCR composition. Alternatively, in order to label the DNA used as a probe with a fluorescent dye, for example, ECL Direct Nucleic Acid Labeling and Detection System (Amersham Pharmacia Biotech, Inc.) may be used.

Many kinds of reagent and temperature conditions are available for conducting hybridization. For example, a pre-hybridization solution which contains 450–900 mM sodium chloride, 45–90 mM sodium citrate, 0.1–1.0% sodium dodecyl sulfate (SDS), and 0–200 µg/ml denatured non-specific DNA and which, in some cases, may optionally contain each 0–0.2% albumin, Ficoll, polyvinylpyrrolidone, or the like, preferably a pre-hybridization solution containing 900 mM sodium chloride, 90 mM sodium citrate, 1% SDS, and 100 µg/ml denatured calf-thymus DNA, is prepared in a volume of 50–200 µl per cm$^2$ of the membrane prepared as above, and the above membrane is immersed and incubated in the solution at 42–68° C. for 1–4 hours, preferably at 45° C. for 2 hours. Then, for example, a hybridization solution which contains 450–900 mM sodium chloride, 45–90 mM sodium citrate, 0.1–1.0% SDS, and 0–200 mg/ml denatured non-specific DNA and which, in some cases, may optionally contain each 0–0.2% albumin, Ficoll, polyvinylpyrrolidone, or the like, preferably a hybridization solution containing 900 mM sodium chloride, 90 mM sodium citrate, 1% SDS, and 100 µg/ml denatured calf-thymus DNA, is mixed with the probe obtained by the above described procedures (at an amount equivalent to $1.0 \times 10^4$–$2.0 \times 10^6$ cpm per cm$^2$ membrane) to prepare a mixed solution in a volume of 50–200 µl per cm$^2$ membrane, and the membrane is immersed and incubated in the mixed solution at 42–68° C. for 4–20 hours, preferably at 45° C. for 16 hours, to achieve hybridization. After the hybridization reaction, the membrane is recovered, and washed 1–4 times each for 10–60 minutes, preferably twice each for 15 minutes, with a washing solution, for example, which contains 15–300 mM sodium chloride, 1.5–30 mM sodium citrate, 0.1–1.0% SDS, and the like, at 42–68° C., preferably with a washing solution containing 300 mM sodium chloride, 30 mM sodium citrate, and 1% SDS at 55° C. Furthermore, the membrane is briefly rinsed with 2×SSC solution (300 mM sodium chloride, 30 mM sodium citrate), and then dried. The positions of DNAs on the membrane that hybridize with the probe used are detected, for example, by subjecting this membrane to autoradiography to detect the positions of the probe on the membrane. The clones corresponding to the positions of the detected DNAs on the membrane are identified on the original agar medium, and can be picked up to isolate clones carrying those DNAs. Specifically, the membrane is exposed to an imaging plate (Fuji Photo Film Co., Ltd.) for 4 hours, and this imaging plate is analyzed using BAS 2000 (Fuji Photo Film Co., Ltd.) to detect signals. From the agar medium used for preparation of the membrane, the parts corresponding to the positions at which signals are detected are cut out as about 5-mm square sections, and these sections are immersed in about 500 µl of SM buffer (50 mM Tris-HCl buffer, pH 7.5, 0.1 M sodium chloride, 7 mM magnesium sulfate, 0.01% gelatin) for 2–16 hours, preferably for 3 hours, to elute the phage particles. The phage particle eluate obtained is spread on agar medium according to the method described in "Molecular Cloning 2nd edition" (J. Sambrook, E. F. Frisch, and T. Maniatis, Cold Spring Harbor Laboratory Press, 1989) 2.60–2.65, and cultured at 37° C. for 6–10 hours. Using this agar medium, phage DNAs are fixed onto a membrane in the same manner as that described above, and this membrane and the above-described probe are used to conduct hybridization. From the sections, of the agar medium used for preparation of the membrane, that correspond to the positions at which signals are detected, phage particles are eluted, spread on agar medium, and used in preparation of membrane in the same manner as that described above, to conduct hybridization. Such identification and purification steps are repeated to obtain a phage clone that carries DNA having a nucleotide sequence which hybridizes to the probe used.

DNA contained in a clone obtained by conducting a screening via hybridization as described above may be subcloned into a plasmid vector which allows easy preparation or analysis of DNA, such as commercially available pUC18, pUC19, pBluescript KS+, or pBluescript KS−, to prepare the plasmid DNA, and its nucleotide sequence can be determined using the dye deoxy terminating method described in, for example, Molecular Cloning: A Laboratory Manual 2nd edition" (1989) (Cold Spring Harbor Laboratory Press) 13.42–13.74. Samples used for nucleotide sequence analysis may be prepared, for example, according to the primer extension method described in, e.g., "Molecular Cloning 2nd edition" (J. Sambrook, E. F. Frisch, and T. Maniatis, Cold Spring Harbor Laboratory Press, 1989) 13.15. Alternatively, in order to analyze the nucleotide sequence, the phage clone may be amplified in NZYM liquid medium according to the method described in, for example, "Molecular Cloning 2nd edition" (J. Sambrook, E. F. Frisch, and T. Maniatis, Cold Spring Harbor Laboratory Press, 1989) 2.60–2.65, to prepare a phage solution. From this phage solution, the phage clone DNA may be then extracted using, for example, Lambda-TRAP PLUS DNA Isolation Kit (Clontech Laboratories, Inc.), and the DNA obtained may be used as a template in the primer extension method described above to prepare samples for nucleotide sequence analysis.

The present terminator DNA is obtained by assaying, as described above, the terminator functions of DNA thus obtained.

In order to express a desired gene using a promoter of the present invention in host cells such as those of plants, a gene in which the promoter of the present invention and the desired gene, and further a terminator as needed, are linked to each other in the form capable of functioning (hereinafter referred to as chimeric gene of the present invention) may be used. In this context, desired genes are those genes to be expressed in host cells such as those of plants, including, for example, genes encoding proteins such as enzymes, storage proteins, receptors, transcriptional factors, or signal transduction factors, and these genes may be suitably linked downstream to the promoter of the present invention in the sense or antisense direction depending on their purposes. Terminators used are not specifically limited as long as they have the function of giving instructions to terminate transcription in host cells into which they are introduced, and may include, for example, the terminator of nopaline synthetic enzyme gene derived from Ti plasmid of *Agrobacterium* (nos-t) and terminators derived from plant viruses such as garlic viruses GV1 and GV2, as well as terminators of the present invention. Furthermore, chimeric genes of the present invention may repeatedly contain the nucleotide sequence of a promoter of the present invention or part thereof. In this context, the phrase "in the form capable of functioning" means that a desired gene contained in the chimeric gene of the present invention has been linked to a promoter of the present invention and/or a terminator in such a way that, when a host cell is transformed by introduction of said chimeric gene, the gene is expressed in the host cell under the control of the promoter and/or the terminator.

Regarding vectors containing a promoter of the present invention, the term "vector" refers to DNA capable of propagating in host cells, including, for example, plasmids, phages, and phagemids which can propagate in cells such as *Escherichia coli*, yeasts, plant cells, or animal cells, and such vectors are appropriately selected depending on the host cell and their purposes. Specific examples may be pUC-based plasmids [such as pUC118, pUC119 (Takara Shuzo Co., Ltd.)], pSC101-based plasmids, Ti plasmids [such as pBI101, pBI121 (Clontech Laboratories, Inc.)], Bluescript phagemids [such as pBluescript SK (+/−) (STRATAGENE)], M13-based phages [such as mp10, mp11 (Amersham Pharmacia Biotech, Inc.)], λ-based phages [such as λ gt10, λ gt11 (Amersham Pharmacia Biotech, Inc.)], or cosmids [such as SuperCos I (STRATAGENE)], and by incorporating a promoter of the present invention into such vector by the usual gene engineering techniques, a vector containing the promoter of the present invention may be constructed.

If, in such vectors containing a promoter of the present invention, a gene insertion site and a terminator further exist downstream from the promoter, the vectors may be preferably used in construction of vectors for expressing a desired gene in host cells. In this context, the term "gene insertion site" refers to, for example, a nucleotide sequence that can be specifically recognized and cleaved by a restriction enzyme commonly used in genetic engineering techniques, and preferably, to a restriction enzyme-recognition nucleotide sequence of the kind that uniquely exists on the vector containing a promoter of the present invention and a terminator. Such gene insertion site, a promoter of the present invention, and a terminator are preferably located such that when a desired gene is inserted into the gene insertion site, the promoter of the present invention, the desired gene, and the terminator are linked together on the vector in the form capable of functioning. Such vector may be constructed, for example, by inserting DNA of a promoter of the present invention into a plasmid containing a gene insertion site and a terminator, and specifically, into the multicloning site (gene insertion site) of pBI101.3 (Clontech Laboratories, Inc.) or the like. Alternatively, it may also be constructed by inserting a promoter of the present invention and a terminator into a vector containing a gene insertion site, and specifically, into the multicloning site (gene insertion site) of pBIN19 (Nucl. Acid. Res. 12:8711–8721 (1984)) or the like.

A vector containing a chimeric gene of the present invention may be preferably used to introduce the chimeric gene into host cells, and may be prepared by cloning the chimeric gene into a vector as described above, or by cloning a desired gene into a gene insertion site on a vector as described above which contains a promoter of the present invention, a gene insertion site, and a terminator. For example, a vector as described above which is prepared using pBI101.3 (Clontech Laboratories, Inc.) may be cleaved with restriction enzymes to remove the reporter gene (β-glucuronidase gene) exists on said vector, and a desired gene may be inserted in place of the reporter gene to prepare a vector containing a chimeric gene of the present invention.

A vector of the present invention as described above may contain a desired gene and/or a terminator in addition to a promoter of the present invention, and it may further contain a marker gene for selecting host cells into which the vector has been introduced (for example, kanamycin resistance gene, hygromycin resistance gene, neomycin resistance gene, a gene capable of conferring herbicide resistance on plants, or the like). Furthermore, the vector may also contain the nucleotide sequence of a promoter of the present invention in repeated form.

A vector of the present invention may be introduced into host cells such as *E. coli* or *Agrobacterium*, for example, by a method such as the calcium chloride method or electroporation method described in, e.g., J. Sambrook, E. F. Frisch, and T. Maniatis, "Molecular Cloning 2nd edition" (1989) (Cold Spring Harbor Laboratory Press). The above microbial cells into which a vector of the present invention has been introduced (transformants) are useful for preparation of a chimeric gene DNA of the present invention or for introduction of the chimeric gene into plant cells.

Alternatively, DNA encoding a promoter of the present invention or DNA of a chimeric gene of the present invention may be introduced into plant cells as host cells, for example, by the particle gun method (a method of direct introduction into plant tissues or cultured cells using a particle gun). Similarly, a vector of the present invention may also be introduced into plant cells as host cells by any of publicly known methods such as *Agrobacterium* infection (a method in which plant tissues are infected with *Agrobacterium*), electrical transfections (electroporation method or electrical transfection method into protoplasts), or the particle gun method.

Among transformants wherein any one of a promoter of the present invention, a chimeric gene of the present invention, or a vector of the present invention has been introduced in host cells, examples of those transformants that are plants may include monocotyledons such as rice, corn, barley, and wheat, and dicotyledons, including legumes such as soybean, pea, bean, and alfalfa; solanaceous plants such as tobacco, tomato, and potato; brassicaceous plants such as cabbage, rape, and leaf mustard; cucurbitaceous plants such as melon, pumpkin and cucumber; umbellifers such as carrot and celery; asteraceous plants such as lettuce.

Transformants may be produced by introducing a promoter of the present invention, a chimeric gene of the present invention, or a vector of the present invention into host cells as described above. For example, host cells in which a promoter of the present invention has been inserted upstream to a desired gene on the genomic DNA and which expresses the desired gene under the control of the promoter of the present invention, or host cells in which a chimeric gene of the present invention has been inserted into the genomic DNA and which expresses the gene contained in the chimeric gene under the control of the promoter of the present invention, or host cells which harbors a vector containing a chimeric gene of the present invention and expresses the gene contained in the chimeric gene under the control of the promoter of the present invention may be obtained.

Plant cells that are transformants thus obtained may be regenerated according to any method used in the usual plant tissue culture techniques described in, for example, S. B. Gelvin, R. A. Schilperoot and D. P. S. Verma, "Plant Molecular Biology Manual" (Kluwer Academic Publishers, 1988); Ko Simamoto and Kiyotaka Okada eds. "Model-Shokubutu-No-Jikken-Protocol (Ine, Shiroinunazuna-Hen) (translation: Experimental protocols for model plants (rice and *Arabidopsis thaliana*))" (Shujun-sha, ISBN4-87962-157-9, C3345, 1996), pp. 78–143; or Hirofumi Uchimiya "Shokubutu-Idenshi-Sosa-Manual: Transgenic-Shokubutu-No-Tukurikata (translation: Plant gene engineering manual: how to produce transgenic plants)" (Kodansha-Scientific, 1990, ISBN4-06-153513-7 C3045), pp. 28–33; and transformed plant thereof derived from said plant cells may be thereby obtained. Furthermore, by growing and inbreeding the plant thus obtained, progenies of the plant may be obtained. In the present invention, all of these are included in transformants.

In order to confirm successful introduction of the desired gene, DNAs may be extracted from the transformants as described above according to the usual gene engineering techniques, cleaved with a restriction enzyme, and used to conduct Southern hybridization with DNA used in transformation of the host cells, or part thereof, as a probe. Similarly, in order to study the expression state of the desired gene, RNAs may be extracted from such transformants according to the usual genetic engineering techniques, and used to conduct Northern hybridization using, as a probe, an oligonucleotide or DNA having the sense or antisense nucleotide sequence of the gene of interest to be expressed under the control of the promoter of the present invention.

Useful traits may be provided to a host organism such as plant by linking a particular gene in the sense direction under the control of promoter of the present invention and expressing it in cells of the host organism. For example, resistance against bacteria, fungi, viruses, insects and the like may be enhanced in tissues of host organisms by expressing a defensive gene such as phenylalanine ammonia lyase gene (PAL), chalcone synthase gene (CHS), chitinase gene (CHT), lysozyme gene or PR protein gene; a disease resistance gene such as Pto gene; a viral coat protein gene; BT (Bacillus thuringiensis) insecticidal protein gene, or the like. Similarly, various protein contents or essential amino acid contents in feed crops may be increased by expressing a storage protein gene such as glycinin gene or β-conglycinin gene of soybean in the host cells; the methionine content or lysine content in feed crops may be increased by expressing, for example, 2S albumin gene of Brazil nut, 10 kDa or 15 kDa protein gene of corn or rice; the biotin content in feed crops may be increased by expressing a biotin biosynthesis-related enzyme gene such as bioA, bioB, bioC, bioD, bioF, or bioH enzyme gene; enhancement of oxidation stability of lipids and improvement of lipids due to decrease in phospholipid content and increase in oleic acid and linolenic acid contents may become possible by expressing, for example, stearoyl-ACP-desaturase gene, acyl-ACP-thioesterase gene, or 3-phosphate acyltransferase gene; or resistance to low temperatures may be enhanced by increasing the proportion of unsaturated fatty acids by expressing an acyltransferase gene in the host cells. An antibiotic resistance useful in selection of transformants may also be provided by expressing a gene involved in the antibiotic resistance such as kanamycin resistance gene, hygromycin resistance gene, or neomycin resistance gene in the host cell. Furthermore, it is also possible to produce a herbicide resistant crop plant by expressing a gene involved in the herbicide resistance such as L-phosphonothricine acetyl transferase or protoporphyrinogen oxidase (PPO) gene in the host cells.

On the other hand, a particular gene may also be linked in the antisense direction under the control of a promoter of the present invention and expressed in cells of a host organism such as a plant to confer a useful trait on the host organism. For example, the starch component of rice seeds may be improved by expressing, in the host cells, an antisense gene against an amylopectin degrading enzyme gene such as that for isomerase of rice; shelf stability of fruits, flower, or the like may be enhanced by expressing, in the host cells, an antisense gene against an ethylene synthetic enzyme gene such as that for 1-aminocyclopropane-1-carboxylate (ACC) synthase of pumpkin or the like; or shelf stability of fruits may also be enhanced by expressing, in the host cells, an antisense gene against polygalacturonase gene of tomato.

Furthermore, fertilities of plants may also be controlled by expressing, in the host cells, a sense or antisense gene of a male sterility-related gene such as S-locus-specific RNase gene.

EXAMPLES

The present invention is illustrated by referring to the following Examples, but the present invention is not limited to such Examples.

Example 1

Isolation of Promoter and Terminator of the Present Invention

A promoter of the present invention and a terminator of the present invention were obtained by conducting inverse polymerase chain reaction (inverse PCR) using genomic DNA prepared from carrot leaves. The procedures are described below.

(1) Preparation of Carrot Genomic DNA

Ten gram of carrot leaves at 6 week-old seeding was ground in liquid nitrogen, suspended in 5 ml of 2×CTAB solution (2% cetyltrimethylammonium bromide, 100 mM Tris-HCl buffer pH 8.0, 20 mM EDTA pH 8.0, 1.4 M sodium chloride, 1% polyvinylpyrrolidone), and then incubated at 55° C. for 10 minutes. To this, an equal volume of chloroform/isoamyl alcohol (24:1) was added, gently mixed for 30 minutes at room temperature, and then centrifuged to recover the upper and lower layers separately. (1) An equal volume of chloroform/isoamyl alcohol (24:1) was added to the upper layer, while (2) an equal volume of 1×CTAB solution (a solution obtained by two-fold diluting 2×CTAB solution with sterile distilled water) was added to the lower layer. After gently mixing each mixture for 10 minutes at room temperature, they were centrifuged again, and the upper layers recovered from (1) and (2) were mixed with each other. To this, a 1/10 volume of 10% CTAB solution (10% cetyltrimethylammonium bromide, 0.7 M sodium chloride) and an equal volume of precipitation buffer (2% cetyltrimethylammonium bromide, 50 mM Tris-HCl buffer pH 8.0, 10 mM EDTA pH 8.0) were added, gently mixed, and then centrifuged. The precipitate was recovered, suspended in 1 M sodium chloride-TE (1 M sodium chloride, 10 mM Tris-HCl buffer pH 8.0, 1 mM EDTA pH 8.0), and an equal volume of isopropanol was further added thereto and gently mixed, followed by centrifugation. The precipitate obtained was rinsed with 70% ethanol, briefly dried, and then suspended in TE. To the suspension, RNase was added to attain a final concentration of 10 μg/ml, incubated at 37° C. for 30 minutes, and then a ¼ volume of 4 M ammonium acetate and two volumes of 100% ethanol were added, mixed, and allowed to stand. DNAs precipitated were recovered by winding them onto a Pasteur pipette, rinsed with 70% ethanol, briefly dried, and suspended in TE (10 mM Tris-HCl buffer pH 8.0, 1 mM EDTA pH 8.0). This DNA solution was appropriately diluted, and subjected to absorbance measurement and agarose gel electrophoresis. As a result, it was confirmed that about 350 μg of genomic DNA had been obtained.

(2) Amplification of DNA Containing Promoter and Terminator of the Present Invention by PCR Ten µg of genomic DNA obtained in (1) was treated with 100 U of Pvu II to digest it completely. A ¹/₁₀ volume of 3 M sodium acetate and two volumes of 100% ethanol were then added, mixed, and centrifuged at 15000 rpm for 10 minutes at 4° C. to recover the precipitated DNA. The precipitate was rinsed with 70% ethanol, and suspended in TE to attain a final concentration of 20 ng/µl. Ligation reaction was conducted using this DNA solution and a ligation kit (Takara Shuzo Co., Ltd.) at a final concentration of 1 ng/µl in a reaction volume of 400 µl, and the reaction mixture was then used as template to conduct PCR (40 cycles of incubation at 94° C. for 1 min, then at 55° C. for 2 min, and further at 74° C. for 3 min per cycle) using oligonucleotides A and B having the following nucleotide sequences:

oligonucleotide A: 5'-GGGTT TCAAT GGATT CGATG-3' (20 mer) and oligonucleotide B: 5'-GCAGA TGCTC AGAAC ACTGC-3' (20 mer).

Furthermore, another PCR (40 cycles of incubation at 94° C. for 1 min, then at 55° C. for 2 min, and further at 74° C. for 3 min per cycle) was conducted using part of the above PCR mixture and oligonucleotides C and D having the following nucleotide sequences:

oligonucleotide C: 5'-GGCAG CTGGC ACCCA TGATA TTTAG AATG-3' (29 mer)

oligonucleotide D: 5'-GGCAG CTGTT CATAA TTTAC AGAGT GAGTG ACAGT CAG-3' (38 mer).

By analyzing part of the reacted solution on 0.8% agarose gel, it was confirmed that a DNA fragment of about 3 kb had been amplified.

The above oligonucleotide A is represented by SEQ ID No:9.

The above oligonucleotide B is represented by SEQ ID No:10.

The above oligonucleotide C is represented by SEQ ID No:11.

The above oligonucleotide D is represented by SEQ ID No:12.

(3) Cloning and Sequencing of Promoter and Terminator of the Present Invention

The PCR mixture obtained in (2) was adjusted to a volume of 200 µl by adding TE. To this solution, an equal amount of neutralized phenol/chloroform/isoamyl alcohol (25:24:1) was added, thoroughly mixed, and then centrifuged at 15,000 rpm for 5 min at 20° C. to recover the upper layer. To this, a ¹/₁₀ volume of 3 M sodium acetate and two volumes of 100% ethanol were added, mixed, and then centrifuged at 15,000 rpm for 10 min at 4° C. to recover the precipitated DNA. After rinsing with 70% ethanol, the DNA was suspended in TE, and treated with 30 U of Pvu II to digest it completely. After the reaction, phenol treatment and ethanol precipitation were conducted as described above. The DNA recovered was suspended in 50 µl of TE, and subjected to Spin Column S-400 (Amersham Pharmacia Biotech, Inc) for purification. Analysis of 1 µl aliquot of eluate from the column on 0.8% agarose gel revealed that there existed DNA fragments of about 2 kb and about 1 kb in size. Two µg of pUC 18 vector was treated with 10 U of Sma I to digest it completely, and further treated with alkaline phosphatase (Takara Shuzo Co., Ltd.) to conduct dephosphorylation. The reaction liquid was subjected to phenol treatment and ethanol precipitation as described above to recover the vector DNA, which was then suspended in TE. Fifty ng of this vector DNA and 50 ng of the fragments described above were subjected to ligation reaction using a ligation kit (Takara Shuzo Co., Ltd.), and then introduced into competent cells of E. coli strain JM109 (Takara Shuzo Co., Ltd.). The bacterial strain that has gone through the introduction step was cultured on LB medium containing 100 µg/ml ampicillin, and plasmid DNAs were prepared from growing clones. By cleaving the DNAs with the restriction enzyme and subjecting them to agarose gel electrophoresis, candidate clones containing desired DNA fragments of about 2 kb and about 1 kb in size were each selected. Using the following oligonucleotides E and F having the nucleotide sequences that exist in pUC18 vector:

oligonucleotide E: 5'-AACAA TTTCA CACAG GAAAC AGCTA TGACC-3' (30 mer)

oligonucleotide F: 5'-CAGTC ACGAC GTTGT AAAAC GACGG CCAGT-3' (30 mer)

as primers, the nucleotide sequences of DNAs carried in the candidate clones were analyzed using Taq Dye Deoxy Terminator Cycle Sequencing Kit (PE Biosystems) and a fluorescence sequencer (PE Biosystems). On the basis of the nucleotide sequences thus revealed, oligonucleotides were synthesized, and used as primers to analyze the nucleotide sequences in the same manner as that described above. As a result, the nucleotide sequence shown in SEQ ID No: 1 and the nucleotide sequence shown in SEQ ID No: 2 were determined.

The above oligonucleotide E is represented by SEQ ID No:13.

The above oligonucleotide F is represented by SEQ ID No:14.

Example 2

Figure 3:
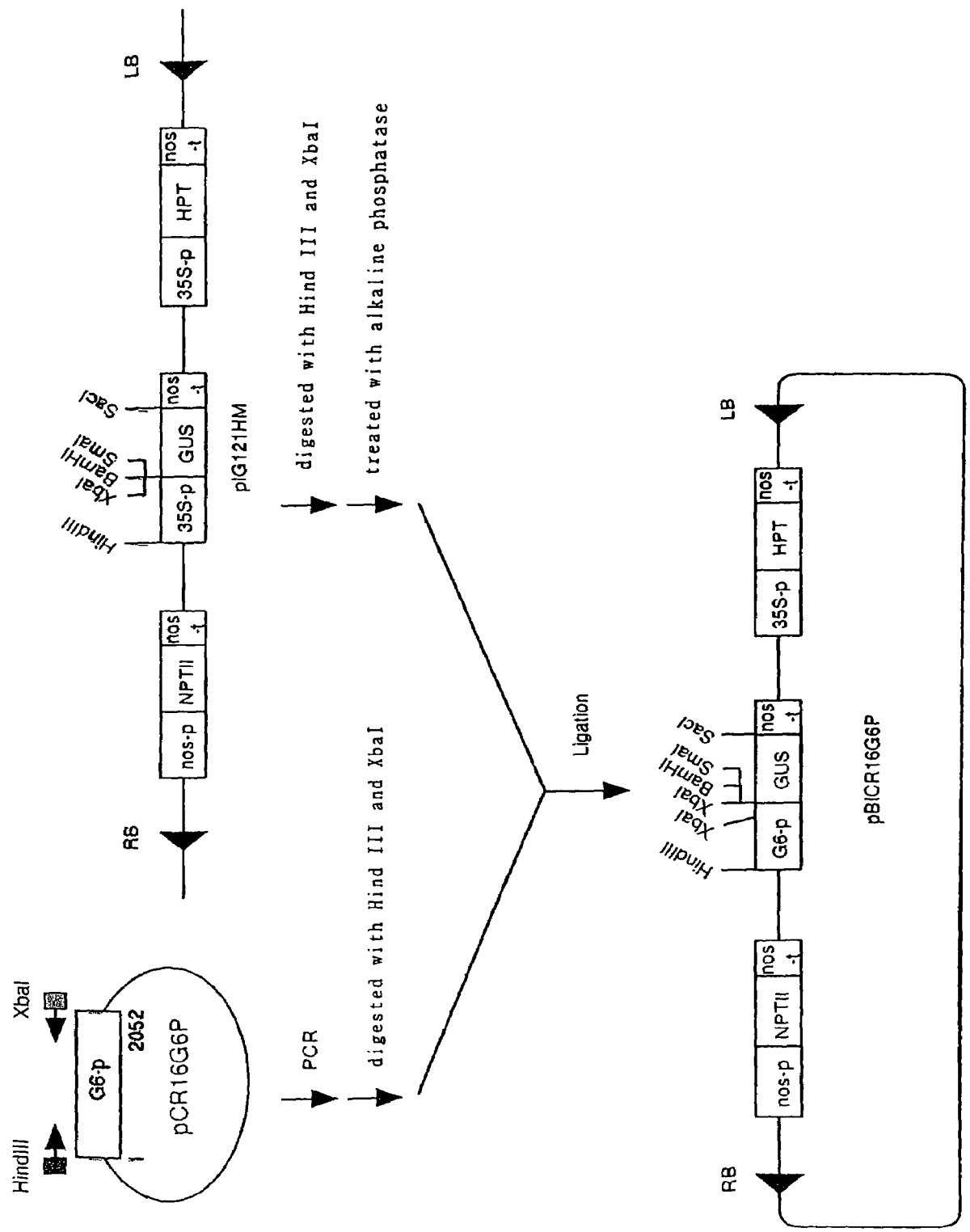
FIG. 3 shows the restriction enzyme map and construction processes of expression vector pBICR16G6P into which a promoter of the present invention has been inserted. "G6-p" indicates the promoter of the present invention. "nos-p" denotes the promoter of nopaline synthetic enzyme gene; "nos-t" denotes the terminator of nopaline synthetic enzyme gene; and "35S-p" denotes the 35S promoter of cauliflower mosaic virus. Likewise, "NPTII" represents kanamycin resistance gene; "GUS" represents β-glucuronidase gene; and "HPT" represents hygromycin resistance gene.

Production of Transgenic Plant into which Promoter of the Present Invention has Been Introduced (1) Construction of Ti Plasmid Expression Vector Oligonucleotides G and H having the following nucleotide sequences that contain restriction enzyme-recognition nucleotide sequences for cloning: oligonucleotide G: 5'-GGAAG CTTCA TGTGT GCCCT ACAGC ACA-3' (28 mer) oligonucleotide H: 5'-GGTCT AGAGA TCTTT AGAAT GTGAT TGCTG-3' (30 mer), were synthesized and used as primers to conduct PCR (40 cycle of incubation at 94° C. for 1 min, then at 55° C. for 2 min, and further at 74° C. for 3 min per cycle) using, as a template, the plasmid having the nucleotide sequence shown in SEQ ID No: 1 that was obtained in Example 1. The amplified DNA fragment was treated with 10 U of Hind III and 10 U of Xba I to digest it completely, and part of the digest was then fractionated on 0.8% agarose gel. The DNA band of about 1.7 kb in size was excised, and DNA contained in the section was purified using glass beads (Bio-Rad Laboratories). Similarly, the remaining solution was fractionated on 4% Nusieve Agarose gel (FMC BioProducts), the band of about 250 bp in size was excised, and DNA contained in the section was purified. Two µg of vector pIG121HM (see FIG. 3), which is derived from pBIN19 described in, e.g., Ohta, S. et al., Plant Cell Physiol. 31(6):805–813 (1990) and Hiei, Y. et al., Plant J. 6:271–282 (1994), was digested with 10 U of Hind III and 10 U of Xba I, and further treated with alkaline phosphatase to conduct dephosphorylation. Phenol treatment and ethanol precipitation were then conducted as described above to recover the vector DNA. After the vector DNA and the above two DNA fragments (about 1.7 kb and about 250 bp) were subjected to ligation reaction using a ligation kit, the ligate was introduced into competent cells of *E. coli* strain HB 101 (Takara Shuzo Co., Ltd.), and the bacterial strain which has gone through the introduction step was cultured on LB medium containing 50 μg/ml kanamycin. Plasmid DNAs were prepared from growing clones, cleaved with restriction enzymes Hind III and Xba I, and analyzed by agarose gel electrophoresis to select a plasmid that contains both the 1.7 kb DNA and the about 250 bp DNA fragment described above. Furthermore, using the selected plasmid as a template, PCR (40 cycles of incubation at 94° C. for 1 min, then at 55° C. for 2 min, and further at 74° C. for 3 min per cycle) was conducted using the aforementioned oligonucleotides G and H as primers: oligonucleotide G: 5'-GGAAG CTTCA TGTGT GCCCT ACAGC ACA-3' (28 mer) oligonucleotide H: 5'-GGTCT AGAGA TCTTT AGAAT GTGAT TGCTG-3' (30 mer). As a result, it was confirmed that a DNA fragment about 2 kb was amplified, and Ti plasmid expression vector pBICR16G6P (FIG. 3) containing the promoter of the present invention upstream from β-glucuronidase gene was thus obtained.

The above oligonucleotide G is represented by SEQ ID No:15.

The above oligonucleotide H is represented by SEQ ID No:16.

(2) Obtaining Transgenic Plant

The transgenic plant was obtained by the method described in S. B. Gelvin, R. A. Schilperoort and D. P. S. Verma, "Plant Molecular Biology/Manual" (1988) (Kluwer Academic Publishers) and Valvekens et al., Proc. Natl. Acad. Sci., 85:5536–5540 (1988).

*Agrobacterium* strain C58C1, which may be prepared from a commercially available standard strain according to the method described in, e.g., Deblaere, R. et al., Nucleic Acids Res. 13:4777–4788 (1985), wad cultured in YEB medium overnight with shaking at 30° C., then inoculated into fresh YEB medium, and further cultured until the turbidity of the culture reached OD600=0.6. The following manipulations were performed in a cold room. The bacterial cells were collected from the culture fluid by centrifugation, suspended in pre-cooled sterile distilled water, and centrifuged again to harvest them. This washing of bacterial cells was repeated twice, and the similar procedure was further performed using 10% glycerol solution instead of sterile distilled water. The bacterial cells thus obtained were suspended in 10% glycerol so as to yield a 400-fold concentrated suspension as compared to the culture fluid. Into the bacterial cell suspension thus prepared, Ti plasmid expression vector pBICR16G6P (see FIG. 1) constructed as described above, which contained the promoter of the present invention, or pIG121HM vector as a control was introduced by electroporation, and the bacterial strain that has gone through the introduction treatment was cultured on a YEB plate containing 50 μg/ml kanamycin. A plasmid DNA was prepared from a growing kanamycin-resistant clone by the alkali-SDS method, and the DNA was analyzed by 0.8% agarose gel electrophoresis. By staining the gel with ethidium bromide to detect DNA bands, it was confirmed that the Ti plasmid expression vector has been introduced. Furthermore, using this plasmid DNA as a template, PCR (40 cycles of incubation at 94° C. for 1 min, then at 55° C. for 2 min, and further at 74° C. for 3 min per cycle) was conducted using the aforementioned oligonucleotides G and H as primers:

oligonucleotide G: 5'-GGAAG CTTCA TGTGT GCCCT ACAGC ACA-3' (28 mer)

oligonucleotide H: 5'-GGTCT AGAGA TCTTT AGAAT GTGAT TGCTG-3' (30 mer).

As a result, amplification of a DNA fragment of about 2 kb was confirmed, verifying that the desired expression vector has been introduced.

The above oligonucleotide G is represented by SEQ ID No:15.

The above oligonucleotide H is represented by SEQ ID No:16.

A section of sterile-cultured tobacco leaf (0.7-cm square) was immersed for 2 minutes in *Agrobacterium* liquid culture incubated overnight at 30° C. in YEB liquid medium containing 50 μg/ml kanamycin, and after removing excess liquid with sterile filter paper, placed on MS-NB medium. After cocultivation for 5 days at 25° C. under the conditions of 16 hours light and 8 hours dark, the section was washed with MS liquid medium, and placed on MS-NBC medium. After culturing for additional 5 days, the section was transferred onto MS-NBCK medium containing 100 μg/ml kanamycin, and stationally cultured for about one month. The regenerated shoot was cut from the leaf section, and subcultured on MS-CK medium. After about one month, the regenerated plants that rooted were planted on soil to obtain self-pollinated seeds.

Example 3

Confirmation of Transgene in Transgenic Plants

The transgenic tobacco seeds was immersed for 5 minutes in 2.5% sodium hypochlorite/0.002% Triton X-100, followed by washing 4 to 5 times with sterile water, and then aseptically germinated by culturing on MS medium containing 100 μg/ml kanamycin. From a plant that exhibited kanamycin resistance, genomic DNA was prepared by the CTAB method. Using 50 ng of this DNA as a template, PCR (40 cycles of incubation at 94° C. for 1 min, then at 55° C. for 2 min, and further at 72° C. for 3 min per cycle) was conducted either using, as primers, a combination of oligonucleotide I comprising a part of the nucleotide sequence of GUS gene, which is a reporter gene, and oligonucleotide J comprising a part of the nucleotide sequence of the promoter of the present invention containing DNA which comprises the nucleotide sequence shown in SEQ ID No: 1 or SEQ ID No: 7:

oligonucleotide I: 5'-ATCAA CACCT CAACA TTGAT GTTAG CGTAC-3' (30 mer)

oligonucleotide J: 5'-TCTGC ATCGG CGAAC TGATC-3' (20 mer)

or using, as primers, a combination of oligonucleotide K comprising a part of the nucleotide sequence of GUS gene, which is a reporter gene, and oligonucleotide L comprising a part of the nucleotide sequence of NOS terminator:

oligonucleotide K: 5'-ACATG TGGAG TGAAG AGTAT C-3' (21 mer)

oligonucleotide L: 5'-GATAA TCATC GCAAG ACCGG-3' (20 mer), and part of the PCR product was fractionated by 0.8% agarose gel electrophoresis. As a result, amplification of desired DNA fragments of about 310 bp and about 400 bp in length, respectively, was confirmed.

The above oligonucleotide I is represented by SEQ ID No:17.

The above oligonucleotide J is represented by SEQ ID No.18.

The above oligonucleotide K is represented by SEQ ID No:19.

The above oligonucleotide L is represented by SEQ ID No:20.

Example 4A

Confirmation of Expression of Transgene

Measurement of GUS activity and GUS staining were conducted in leaves and roots of seedling of the transgenic plant obtained in Example 2 according to the methods described in Jefferson, Plant Mol. Biol. Rep. 5:387–405 (1987). The GUS activity was measured by fluorometry using 4-methylumbelliferyl glucuronide as a substrate, and the activity staining was conducted using 5-bromo-4-chloro-3-indolyl-β-D-glucuronide (X-Gluc) as a substrate, and the amount of deposited blue dye (indigotin) was measured.

(1) GUS Staining

The above-described transgenic tobacco seeds were aseptically germinated by culturing them on MS medium containing 100 μg/ml kanamycin. After 1 week, 3 weeks, or 1 month, the kanamycin-resistant plant was pulled out, and immersed overnight in GUS staining solution (1 mM X-Gluc, 0.5 mM $K_3Fe(CN)_6$, 0.5 mM $K_4Fe(CN)_6$, 0.3% Triton X-100) at 37° C. to allow the reaction to proceed. After the reaction, it was decolorized with 100% ethanol, and the staining pattern was observed. As a result, in the transgenic tobacco into which Ti plasmid expression vector pBICR16G6P (see FIG. 1) containing the promoter of the present invention, β-glucuronidase gene linked downstream to the promoter of the present invention on the expression vector was highly expressed in the leaf, root, and stem.

(2) GUS Activity Measurement

The above-described transgenic tobacco seeds were aseptically germinated on a medium containing 100 μg/ml kanamycin, and further cultured at 25° C. One week, three weeks, or one month after the germination, 0.8 g of root and 0.5 g of leaf from the kanamycin-resistant plant were sampled into mortars, supplemented with 1 ml and 0.5 ml, respectively, of extraction buffer (50 mM phosphate buffer pH 7.0, 10 mM EDTA, 0.1% Triton X-100, 0.1% sarcosyl, 10 mM mercaptoethanol), and ground with appropriate amount of added sea sand. The ground liquid was transferred into an Eppendorf tube, centrifuged, and the supernatant was recovered. Ten to seventy μl of this liquid was added to 500 μl of the reaction substrate solution (50 mM phosphate buffer pH 7.0, 10 mM EDTA, 0.1% Triton X-100, 0.1% sarcosyl, 10 mM mercaptoethanol, 1 mM 4-methylumbelliferyl-β-D-glucuronide), and incubated at 37° C. One hundred μl aliquots of the reaction liquid were sampled at regular intervals, and 900 μl of stop solution (0.2 M sodium carbonate solution) was immediately added thereto and mixed. Fluorescence of the samples thus prepared was measured in a spectrophotofluorometer (HITACHI, Ltd. F-2000) (excitation wavelength: 365 nm, emission wavelength: 455 nm). From the measured value and the protein concentration of the extract from leaf or root, the GUS activity was calculated. The results are shown in Table 1. Quantification of protein concentration was performed by a method using Bio-Rad Laboratories Protein assay reagent. The GUS activity was detected in the samples of leaf and root from the transgenic tobacco into which Ti plasmid expression vector pBICR16G6P containing a promoter of the present invention (the vector contains DNA comprising a promoter of the present invention linked to β-glucuronidase gene) has been introduced. One of the transformants with the highest GUS activity exhibited 8-fold higher GUS activity comparing the control transformant which was transformed with pIG121HM vector (the vector contains DNA comprising 35S promoter linked to β-glucuronidase gene).

Table 1: Results of GUS activity measurement of transgenic tobacco [IP-8 to 14 represent tobacco individuals into which Ti plasmid expression vector pBICR16G6P containing the promoter of the present invention has been introduced, and PIG-1 to 2 represent tobacco individuals into which pIG121HM vector has been introduced. Relative ratio is the relative value of GUS activity in leaf or root at each developmental stage, wherein corresponding activity of pIG121HM vector-transformed tobacco (PIG-2) is considered as 1.]

| Tobacco individual | GUS activity (pmol-MU/min/mg-protein) | | | |
|---|---|---|---|---|
| | Leaf ($\times 10^4$) | Relative ratio | Root ($\times 10^4$) | Relative ratio |
| 1 week post-seeding | | | | |
| Present Invention (IP-8) | 1.40 | 1.9 | 1.70 | 1.4 |
| Present Invention (IP-9) | 1.10 | 1.5 | 1.10 | 0.9 |
| Present Invention (IP-10) | 1.00 | 1.4 | 1.40 | 1.2 |
| Present Invention (IP-11) | 1.20 | 1.6 | 1.30 | 1.1 |
| Present Invention (IP-12) | 1.60 | 2.2 | 2.40 | 2.0 |
| Present Invention (IP-13) | 1.70 | 2.3 | 1.70 | 1.4 |
| Present Invention (IP-14) | 0.64 | 0.9 | 0.68 | 0.6 |
| Comparative Example (PIG-1) | 0.71 | 1.0 | 1.00 | 0.8 |
| Comparative Example (PIG-2) | 0.74 | 1.0 | 1.20 | 1.0 |
| non-transformed strain SR1 | 0.00 | 0.0 | 0.00 | 0.0 |
| 3 weeks post-seeding | | | | |
| Present Invention (IP-8) | 1.90 | 2.7 | 3.60 | 1.6 |
| Present Invention (IP-9) | 1.20 | 1.7 | 2.30 | 1.0 |
| Present Invention (IP-10) | 2.20 | 3.1 | 5.00 | 2.3 |
| Present Invention (IP-11) | 1.40 | 2.0 | 3.00 | 1.4 |
| Present Invention (IP-12) | 2.80 | 3.9 | 6.00 | 2.7 |
| Present Invention (IP-13) | 1.40 | 2.0 | 4.30 | 2.0 |
| Present Invention (IP-14) | 1.80 | 2.5 | 6.80 | 3.1 |
| Comparative Example (PIG-1) | 1.00 | 1.4 | 1.90 | 0.9 |
| Comparative Example (PIG-2) | 0.71 | 1.0 | 2.20 | 1.0 |
| non-transformed strain SR1 | 0.00 | 0.0 | 0.00 | 0.0 |
| 1 month post-seeding | | | | |
| Present Invention (IP-8) | 1.50 | 2.9 | 2.60 | 2.6 |
| Present Invention (IP-9) | 1.00 | 2.0 | 1.00 | 1.0 |
| Present Invention (IP-10) | 1.10 | 2.2 | 2.80 | 2.8 |
| Present Invention (IP-11) | 0.90 | 1.8 | 1.40 | 1.4 |
| Present Invention (IP-12) | 3.40 | 6.7 | 8.40 | 8.4 |
| Present Invention (IP-13) | 1.50 | 2.9 | 3.60 | 3.6 |
| Present Invention (IP-14) | 1.20 | 2.4 | 2.50 | 2.5 |
| Comparative Example (PIG-1) | 0.09 | 0.2 | 0.88 | 0.9 |
| Comparative Example (PIG-2) | 0.51 | 1.0 | 1.00 | 1.0 |
| non-transformed strain SR1 | 0.00 | 0.0 | 0.00 | 0.0 |

Example 4B

Confirmation of Expression of Transgene (1) Obtaining Transgenic Plant

The other transgenic plant, *Arabidopsis*, was conducted according to the basically same method as the above example in which *Agrobacterium* strain C58C1 having the Ti plasmid expression vector pBICR16G6P was used to introduce the vector into the target plant.

After being aceptically germinated, a section (ca. 1 cm) of *Arabidopsis* root grown on MS medium at 23° C. for 2–3 weeks was cultured on CIM agar medium for 2 days, and then it was immersed for 2 minutes in *Agrobacterium* liquid culture incubated overnight at 30° C. in YEB liquid medium containing 50 µg/ml kanamycin, and after removing excess liquid with sterile filter paper, placed on CIM agar medium. After culturing for 2, days, the section was transferred onto SIMC agar medium. After further culturing for 2 days, the section was transferred onto SIMCH agar medium. The regenerated shoot was cut from the root section, and subcultured on MS medium. After about one month, the individuals that rooted were planted on soil or rock wool and grown in an growth chamber to obtain inbred seeds.

(2) Confirmation of Transgene in Transgenic Plant

The transgenic *Arabidopsis* seeds was immersed for 5 minutes in 1.0% sodium hypochlorite, followed by washing 3 to 5 times with sterile water, and then aseptically germinated on MS medium containing 20 µg/ml hygromycin. From 4 or 5 rosette leaves obtained from an individual that exhibited hygromycin resistance, genomic DNA was prepared by the CTAB method. Using 50 ng of this DNA as a template, PCR (40 cycles of incubation at 94° C. for 1 min, then at 55° C. for 2 min, and further at 72° C. for 3 min per cycle) was conducted either using, as primers, a combination of oligonucleotide I comprising a part of the nucleotide sequence of GUS gene, which was a reporter gene, and oligonucleotide J comprising a part of the nucleotide sequence of the promoter of the present invention containing DNA which comprises the nucleotide sequence shown in SEQ ID No: 7:

oligonucleotide I: 5'-ATCAA CACCT CAACA TTGAT GTTAG CGTAC-3' (30 mer)

oligonucleotide J: 5'-TCTGC ATCGG CGAAC TGATC-3' (20 mer)

or using, as primers, a combination of oligonucleotide K comprising a part of the nucleotide sequence of GUS gene, which is a reporter gene, and oligonucleotide L comprising a part of the nucleotide sequence of NOS terminator:

oligonucleotide K: 5'-ACATG TGGAG TGAAG AGTAT C-3' (21 mer)

oligonucleotide L: 5'-GATAA TCATC GCAAG ACCGG-3' (20 mer), and part of the PCR product was fractionated by 0.8% agarose gel electrophoresis. As a result, amplification of desired DNA fragments of about 310 bp and about 400 bp in length, respectively, was confirmed.

The above oligonucleotide I is represented by SEQ ID No:17.

The above oligonucleotide J is represented by SEQ ID No.18.

The above oligonucleotide K is represented by SEQ ID No:19.

The above oligonucleotide L is represented by SEQ ID No:20.

(3) Confirmation of Expression of Transgene

Measurement of GUS activity and GUS staining were conducted in leaves and roots of seedling of the transgenic plant obtained in Example 4B (1) and (2) according to the methods described in Jefferson, Plant Mol. Biol. Rep. 5:387–405 (1987). The GUS activity was measured by fluorometry using 4-methylumbelliferyl glucuronide as a substrate, and the activity staining was conducted using 5-bromo-4-chloro-3-indolyl-β-D-glucuronide (X-Gluc) as a substrate, and the amount of deposited blue dye (indigotin) was measured.

(3-1) GUS Staining

The above-described transgenic Arbidopsis seeds were aseptically germinated by culturing them on MS medium containing 20 µg/ml hygromycin. After 3 weeks, the hygromycin-resistant plant was pulled out, and immersed overnight in GUS staining solution (1 mM X-Gluc, 0.5 mM $K_3Fe(CN)_6$, 0.5 mM $K_4Fe(CN)_6$, 0.3% Triton X-100) at 37° C. to allow the reaction to proceed. After the reaction, it was decolorized with 100% ethanol, and the staining pattern was observed. As a result, in the transgenic *Arabidopsis* into which Ti plasmid expression vector pBICR16G6P (see FIG. 1) containing the promoter of the present invention, β-glucuronidase gene linked downstream to the promoter of the present invention on the expression vector was highly expressed in the leaf, root, and stem.

(3-2) GUS Activity Measurement

The above-described transgenic *Arabidopsis* seeds were aseptically germinated by culturing them on a medium containing 20 µg/ml hygromycin, and further cultured at 23° C. Three weeks after the seeding, roots and leaves obtained from three individuals that exhibited hygromycin resistance were sampled into mortars, supplemented with 1 ml and 1 ml, respectively, of extraction buffer (50 mM phosphate buffer pH 7.0, 10 mM EDTA, 0.1% Triton X-100, 0.1% sarcosyl, 10 mM mercaptoethanol), and ground with appropriate amount of added sea sand. The ground liquid was transferred into an Eppendorf tube, centrifuged, and the supernatant was recovered. Ten to seventy µl of this liquid was added to 500 µl of the reaction substrate solution (5.0 mM phosphate buffer pH 7.0, 10 mM EDTA, 0.1% Triton X-100, 0.1% sarcosyl, 10 mM mercaptoethanol, 1 mM 4-methylumberlliferyl-β-D-glucuronide), and incubated at 37° C. One hundred µl aliquots of the reaction liquid were sampled at regular intervals, and 900 µl of stop solution (0.2 M sodium carbonate solution) was immediately added thereto and mixed. Fluorescence of the samples thus prepared was measured in a spectrophotofluorometer (HITACHI, Ltd. F-2000) (excitation wavelength: 365 nm, emission wavelength: 455 nm). From the measured value and the protein concentration of the extract from leaf or root, the GUS activity was calculated. Quantification of protein concentration was performed by a method using Bio-Rad Laboratories Protein assay reagent. As a result, the GUS activity was detected in the samples of leaves and roots from the transgenic *Arabidopsis* into which Ti plasmid expression vector pBICR16G6P containing the promoter of the present invention (the vector contains DNA comprising the promoter of the present invention linked to β-glucuronidase gene) has been introduced. Some of the transformants exhibited several-fold higher GUS activity comparing the control transformant which was transformed with pIG121HM vector (the vector contains DNA comprising 35S promoter linked to β-glucuronidase gene).

Example 5

Production of Transgenic Plant into which Promoter of the Present Invention has been Introduced and Confirmation of Expression of Transgene As showed in Example 2 (1), the bacterial clone harboring pBICR16G6P vector was cultured over night at 37° C. with 2 ml of LB medium including 50 µg/ml of kanamycin. Then, pre-culture was inoculated to the 500 ml of LB medium including 50 µg/ml of kanamycin and cultured over night 37° C. The bacterial cell was collected by centrifugation at 8000 rpm for 10 minutes and the vector DNA was purified using QIAGEN plasmid purification kit (QIAGEN, Inc.).

The recovered vector was introduced to the soybean expanded leaf excised from the plant grown in greenhouse and the soybean somatic embryo induced and cultured according to the method described by Finer J. and Nagasawa A. (Plant Cell, Tissue and Organ Culture, 15, 125–136, 1988) using the gene bombardment method (C.M.Particle Gun System, Rehbock Co., Tokyo, Japan: Yang N-S, Christou P, Particle Bombardment Technology for Gene Transfer, W. H. Freeman and Co. Publishers, New York, pp. 52–59). The gold particles (Tokuriki Honten Co., Ltd, Japan) of 0.5~1 µm were washed several times with ethanol and prepared 60 mg/ml gold particle suspension with sterilized water. Fifty µl of the gold particle suspension, 50 µl of 2.5M $CaCl_2$, 20 µl of 0.1M spermidine were mixed to the 20 µl of pBICR16G6P vector suspension (0.5 µg/ml). After standing for 30 minutes at room temperature, the gold particles were recovered by the centrifugation at 9000 rpm for 10 seconds and suspended to 65 µl of 75% ethanol. The gold particles were recovered by the centrifugation at 9000 rpm for 10 seconds and resuspended to 300 µl of 100% ethanol. This gold particle suspension was sonicated (TOMY SEIKO Co., Ltd.) and 20 µl of suspension was transferred to the projectile (Rehbock Co., Ltd. Tokyo, Japan) and dried (10 µl of suspension was transferred twice). This gold particles were bombarded twice to the soybean expanded leaf or somatic embryo on the MS agar medium under the 10 mmHg, 335 m/sec condition.

For the control experiment, pBI121 and pBI221 (Clontech Laboratories, Inc.) were bombarded to the soybean expanded leaf or somatic embryo as described. After the gene bombardment, the soybean expanded leaf or somatic embryo were left at 25° C. for 24 hr and then soaked with GUS staining buffer (1 mM X-Gluc, 0.5 mM $K_3Fe(CN)_6$, 0.5 mM $K_4Fe(CN)_6$, 0.3% Triton X-100) at 37° C. for over night. The blue spots derived from GUS expression were observed on somatic embryo, as well as expanded leaf after de-staining with 100% ethanol in the room temperature. Therefore, strong GUS activity of pBICR16G6P vector was confirmed both in the soybean expanded leaf and somatic embryo.

Example 6

Construction of Vector Containing Promoter and Terminator of the Present Invention In this Example, the hereinbelow mentioned oligonucleotide P is represented by SEQ ID No:21 and oligonucleotide Q is represented by SEQ ID No. 22.

(1) Construction of Ti Plasmid Derivative (pBI Δ)

Figure 4:
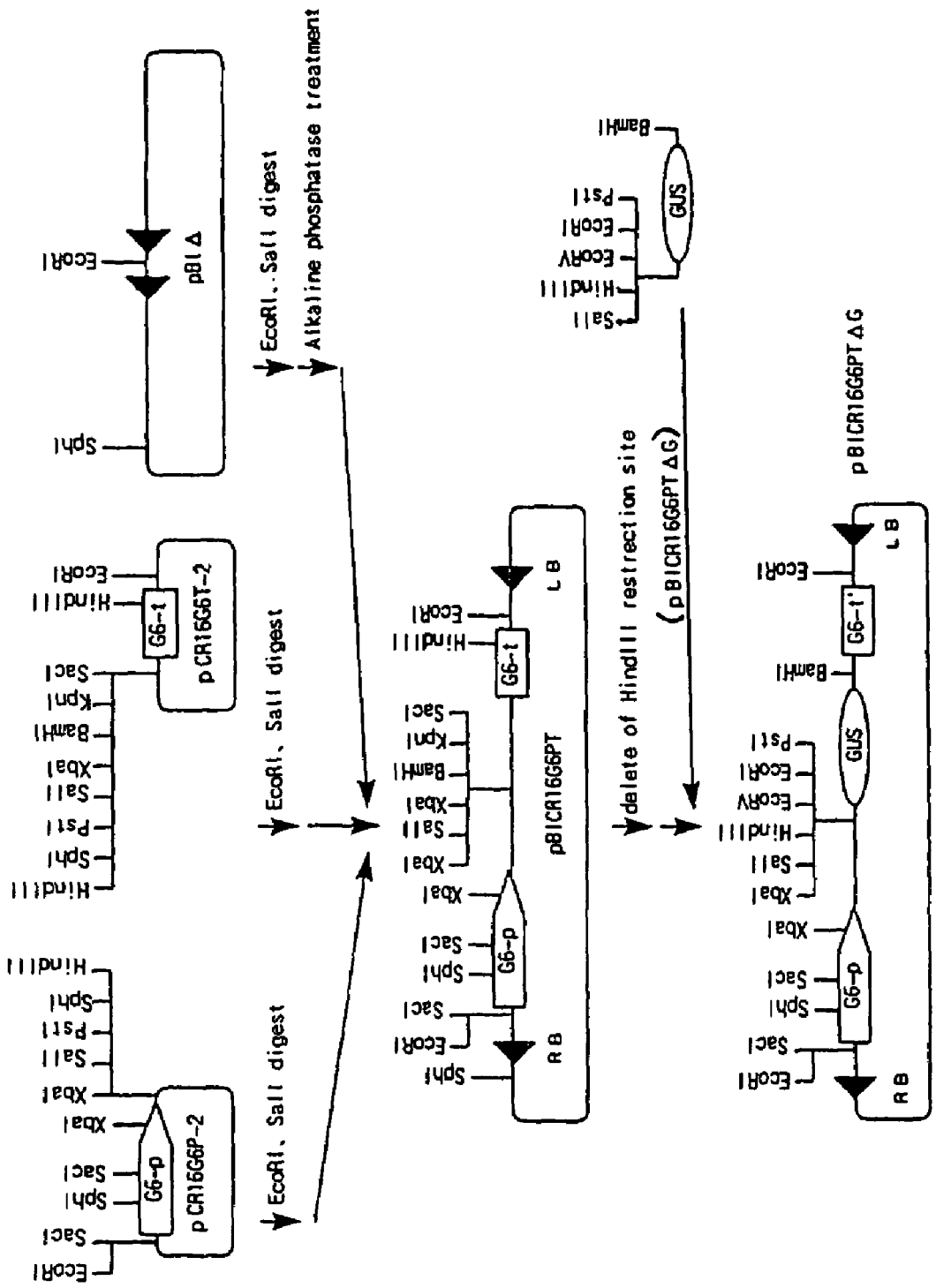
FIG. 4 shows the restriction enzyme map and construction process of expression vector pBICR16G6PT Δ G into which a promoter and a terminator of the present invention have been inserted. "G6-p" indicates the promoter of the present invention, and "G6-t" indicates the terminator of the present invention. "G6-t'" denotes the terminator derived from "G6-t" whose HindIII cutting site has been deleted. "RB" means the right border sequence and "LB" means the left border sequence that locate on the binary vector. "GUS" represents β-glucuronidase gene.

To construct of the plant expression vector containing a promoter and a terminator of the present invention, as a first step, Ti plasmid derivative (pBI Δ) was constructed as shown in FIG. 4. Oligonucleotides P and Q having the following nucleotide sequences that contain restriction enzyme-recognition nucleotide sequences for cloning:

oligonucleotide P: 5'-GGGAA TTCTC AGATT GTCGT TTCCC GCCTT CAG-3'(33mer)

oligonucleotide Q: 5'-CAGAT CTGGG GAACC CTGTG GTTG-3'(24mer)

were synthesized and used as primers to conduct PCR (40 cycle of incubation at 94° C. for 1 min, then at 55° C. for 2 min, and further at 74° C. for 3 min per cycle) using, as a template, 5 ng of pBI101 vector (Clontech Laboratories, Inc.). The amplified DNA fragment was treated with 30 U of EcoRI and 30 U of Sph I to digest it completely, and part of the digest was then fractionated on 4.0% Nusieve Agarose gel (FMC BioProducts). The DNA band of 186 bp in size was excised, and DNA contained in the section was purified using glass beads (Bio-Rad Laboratories). Two µg of vector pBI101 (Clontech Laboratories, Inc.) was digested with 10 U of EcoRI and 10 U of Sph I. Phenol treatment and ethanol precipitation were then conducted as described above to recover the vector DNA. After the vector DNA and the above DNA fragment was subjected to ligation reaction using a ligation kit, the ligate was introduced into competent cells of *E. coli* strain HB101 (Takara Shuzo Co., Ltd.), and the transformed bacterial cell was cultured on LB medium plate containing 50 µg/ml kanamycin. Plasmid DNAs were prepared from growing clones, cleaved with restriction enzymes EcoR I and Sph I, and analyzed by agarose gel electrophoresis to select a plasmid (pBI Δ) that contained 186 bp DNA fragment described above. EcoR I site is the only one restriction enzyme recognition site in the T-DNA region of this plasmid.

(2) Introduction of Hind III and Xba I Recognition Sites to pCR 16G6P Containing a Promoter of the Present Invention In this Example, the hereinbelow mentioned oligonucleotide R is represented by SEQ ID No:23 and oligonucleotide S is represented by SEQ ID No. 24.

Oligonucleotides R and S having the following nucleotide sequences that contain restriction enzyme-recognition nucleotide sequences for cloning:

oligonucleotide R: 5'-GGTCT AGAGA TCTTT AGAAT GTGAT TGCTG-3' (30 mer)

oligonucleotide S: 5'-AACAA TGTAT GTCCG GTGTA CATCT ATGAC-3' (30 mer)

were synthesized and used as primers to conduct PCR (40 cycle of incubation at 94° C. for 1 min, then at 55° C. for 2 min, and further at 74° C. for 3 min per cycle) using, as a template, the plasmid having the nucleotide sequence shown in SEQ ID No: 7 that was obtained in Example 1. The amplified DNA fragment was treated with 50 U of Xba I to digest it completely, and part of the digest was then fractionated on 4.0% Nusieve Agarose gel (FMC BioProducts). The DNA band of about 250 bp in size was excised, and DNA contained in the section was purified using glass beads (Bio-Rad Laboratories). Two µg of pCR16G6P vector having the nucleotide sequence shown in SEQ ID No: 7 that was obtained in Example 1 was digested with 10 U of Xba I, and further treated with alkaline phosphatase to conduct dephosphorylation. Phenol treatment and ethanol precipitation were then conducted as described above to recover the vector DNA. After the vector DNA and the recovered 250 bp DNA fragment was subjected to ligation reaction using a ligation kit, the ligate was introduced into competent cells of *E. coli* strain HB101 (Takara Shuzo Co., Ltd.), and the transformed bacterial cell was cultured on LB medium containing 50 μg/ml kanamycin. Plasmid DNA was prepared from growing clones, cleaved with restriction enzyme Xba I, and analyzed by agarose gel electrophoresis to select a plasmid that contained 250 bp DNA fragment described above. Furthermore, using the selected plasmid as a template and using the aforementioned oligonucleotides S as a primer:

oligonucleotide S: 5'-AACAA TGTAT GTCCG GTGTA CATCT ATGAC-3' (30 mer)

the nucleotide sequence carried in the selected plasmid was also analyzed using Taq Dye Deoxy Terminator Cycle Sequencing Kit (PE Biosystems) and a fluorescence sequencer (PE Biosystems). As a result, it was confirmed that this plasmid, pBICR16G6P-2 (FIG. 4) contained the promoter of the present invention upstream from β-glucuronidase gene.

(3) Construction of the Vector Containing a Terminator of the Present Invention pCR16G6T-2 containing a terminator nucleotide sequence of the present invention, which is added Sac I and EcoR I recognition sites for gene cloning was constructed using pCR16G6T containing the DNA fragment in SEQ ID No: 2. Fifty ng of pC16 plasmid DNA (Plant Cell Physiology, 38(9):1080–1086 (1997), JP 07-188288) was treated with 50U of Dra I and 50U of Sac I to digest it completely, and part of the digest was then fractionated on 4.0% Nusieve Agarose gel (FMC BioProducts). The DNA band of about 189 bp in size was excised, and DNA contained in the section was purified using glass beads (Bio-Rad Laboratories).

The hereinbelow mentioned oligonucleotide T is represented by SEQ ID No:25 and the oligonucleotide U is represented by SEQ ID No:26.

Oligonucleotides T and U having the following nucleotide sequences that contain restriction enzyme-recognition nucleotide sequences for cloning:

oligonucleotide T: 5'-TTCAT AATTT ACAGA GTGAG TGACA GTCAG-3'(30mer)

oligonucleotide U: 5'-GGGAA TTCCT GAAAA GGAAG TTCAT CGATC TATC-3'(34mer)

were synthesized and used as primers to conduct PCR (40 cycle of incubation at 94° C. for 1 min, then at 55° C. for 2 min, and further at 74° C. for 3 min per cycle) using, as a template, 5 ng of pCR16G6T containing the DNA fragment in SEQ ID No: 2. The amplified DNA fragment was treated with 20 U of EcoRI and 20 U of Dra I to digest it completely, and part of the digest was then fractionated on 4.0% Nusieve Agarose gel (FMC BioProducts). The DNA band of 800 bp in size was excised, and DNA contained in the section was purified using glass beads (Bio-Rad Laboratories). Two μg of vector pUC18 (Takara Shuzo Co., Ltd.) was digested with 20 U of EcoRI and 20 U of Dra I. Phenol treatment and ethanol precipitation were then conducted as described above to recover the vector DNA. After the vector DNA and the above two DNA fragments were subjected to ligation reaction using a ligation kit, the ligate was introduced into competent cells of *E. coli* strain JM109 (Takara Shuzo Co., Ltd.), and the transformed bacteria was cultured on LB medium containing 100 μg/ml of ampicillin and 40 μg/ml of X-Gal. Vector DNAs were prepared from white colony and cleaved with restriction enzymes EcoR I and Sac I, and analyzed by agarose gel electrophoresis to select a vector (pCR16G6T-2) containing 989 bp DNA fragment.

(4) Construction of Ti Plasmid Vector Containing a Promoter and a Terminator of the Present Invention Two μg of pCR16G6P-2 described in this Example 6 (2) was treated with 20 U of EcoRI and 20 U of Sal I to digest it completely, and part of the digest was then fractionated on 0.8% Agarose gel (Dojindo Laboratories). The DNA band of 2 kb in size was excised, and DNA fragment G contained in the section was purified using glass beads (Bio-Rad Laboratories). Similarly, Two μg of pCR16G6T-2 described in this Example 6 (3) was digested completely with 20 U of EcoRI and 20 U of Sal I and part of the digest was then fractionated on 4% Nusieve Agarose gel (FMC BioProducts). The DNA band of 1 kb in size was excised, and DNA fragment H contained in the section was purified using glass beads (Bio-Rad Laboratories). Also pBluescript KS vector (Clontech Laboratories, Inc.) was treated with EcoR I to digest it completely and further treated with alkaline phosphatase to conduct dephosphorylation. Phenol treatment and ethanol precipitation were then conducted as described above to recover the vector DNA. The vector DNA and the above two DNA fragments, H and G were subjected to ligation reaction using a ligation kit, the ligate was introduced into competent cells of *E. coli* strain JM109 (Takara Shuzo Co., Ltd.), and the transformed bacteria was cultured on LB medium containing 100 μg/ml of ampicillin and 40 μg/ml of X-Gal. Vector DNAs were prepared from white colonies and cleaved with restriction enzyme EcoR I, and analyzed by 0.8% agarose gel electrophoresis to select a vector containing 3 kb DNA fragment. This vector was then treated with 20U of EcoR I to digest it completely. On the other hand, pBI Δ described in (1) was treated with 20U of EcoR I to digest it completely and further treated with alkaline phosphatase to conduct dephosphorylation (Takara Shuzo Co., Ltd.). After the vector DNA and 3 kb DNA fragments were subjected to ligation reaction using a ligation kit, the ligate was introduced into competent cells of *E. coli* strain HB101 (Takara Shuzo Co., Ltd.), and the transformed bacterial cell was cultured on LB medium containing 50 μg/ml of kanamycin. Vector DNAs were prepared from growing clones and cleaved with restriction enzymes EcoR I or EcoR I and Sal I, and analyzed by 0.8% agarose gel electrophoresis to select a vector (pBICR16G6PT) containing 3 kb DNA fragment or about 2 kb and 1 kb DNA fragment respectively.

(5) Deletion of Hind III Recognition Site from pBICR16G6PT

One μg of pBICR16G6PT was treated with Hind III to digest it completely and recovered DNA by the ethanol precipitation. Then, this DNA fragment was treated with 5U of T4 DNA polymerase (Takara Shuzo Co., Ltd.) to make blunt ends and phenol treatment and ethanol precipitation were then conducted as described above to recover the DNA fragment. This DNA fragment was subjected to ligation reaction using a ligation kit, the ligate was introduced into competent cells of *E. coli* strain HB101 (Takara Shuzo Co., Ltd.), and the transformed bacteria was cultured on LB medium containing 50 μg/ml of kanamycin. Vector DNAs were prepared from growing clones and cleaved with restriction enzyme Hind III, and analyzed by 0.8% agarose gel electrophoresis to select a vector (pBICR16G6PT Δ) that lost the Hind III recognition site.

Example 7

Confirmation of Expression of Transgene (1) Introduction of GUS Gene to pBICR16G6PT Δ

Two μg of pBI221 plasmid DNA (Clontech Laboratories, Inc.) was treated with 20U of Sma I and 20U of Sac I to digest it completely and DNA was recovered by the ethanol precipitation. Then, this DNA fragment was treated with 5U of T4 DNA polymerase (Takara Shuzo Co., Ltd.) to make blunt ends and phenol treatment and ethanol precipitation were then conducted as described above to recover the DNA fragment. DNA fragment was then fractionated on 1.0% Agarose gel (Dojindo Laboratories). The DNA band of about 1.7 kb in size was excised, and GUS gene contained in the section was purified using glass beads (Bio-Rad Laboratories). Also two μg of pBluescript KS vector (Clontech Laboratories, Inc.) was treated with 20U of Sma I to digest it completely and further treated with alkaline phosphatase to conduct dephosphorylation. Phenol treatment and ethanol precipitation were then conducted as described above to recover the vector DNA fragment. Fifty μg of vector DNA and 100 ng of above 1.7 kb GUS gene fragment was subjected to ligation reaction using a ligation kit, the ligate was introduced into competent cells of *E. coli* strain JM109 (Takara Shuzo Co., Ltd.), and the transformed bacterial cell was cultured on LB medium containing 100 μg/ml of ampicillin and 40 μg/ml of X-Gal.

The hereinbelow mentioned oligonucleotide M is represented by SEQ ID No:27 and the oligonucleotide K is represented by SEQ ID No:19.

Oligonucleotides M and K having the following nucleotide sequences that contain nucleotide sequence based on pBluescript KS (oligonucleotide K) and GUS gene (oligonucleotide M):

oligonucleotide M: 5'-GTAAA ACGAC GGCCA GT-3' (17mer)

oligonucleotide K: 5'-ACATG TGGAG TGAAG AGTAT-3' (21mer)

were synthesized and used as primers to conduct PCR (40 cycle of incubation at 94° C. for 1 min, then at 55° C. for 2 min, and further at 74° C. for 3 min per cycle) with white colony suspension of above transformants. The amplified DNA fragment was then fractionated on 4.0% Nusieve Agarose gel (FMC BioProducts). The clone showed the 410 bp DNA fragment amplification was selected for further construction. Two μg of purified plasmid DNA was treated with 20U of Sal I and 20U of BamH I to digest it completely and DNA fragment was then fractionated on 0.8% Agarose gel (Dojindo Laboratories). The DNA band of about 1.7 kb in size was excised, and DNA fragment contained in the section was purified using glass beads (Bio-Rad Laboratories). Two μg of pBICR16G6PT Δ was digested with 20U of Sal I and 20U of BamH I and further treated with alkaline phosphatase to conduct dephosphorylation (Takara Shuzo Co., Ltd.). Fifty ng of vector DNA and 20 ng of above 1.7 kb DNA fragment were subjected to ligation reaction using a ligation kit, the ligate was introduced into competent cells of *E. coli* strain HB101 (Takara Shuzo Co., Ltd.), and the transformed bacteria was cultured on LB medium containing 50 μg/ml of kanamycin.

Oligonucleotides U and K having the following nucleotide sequences as described:

oligonucleotide U: 5'-GGGAA TTCCT GAAAA GGAAG TTCAT CGATC TATC-3'(34mer)

oligonucleotide K: 5'-ACATG TGGAG TGAAG AGTAT-3' (21mer)

were synthesized and used as primers to conduct PCR (40 cycle of incubation at 94° C. for 1 min, then at 55° C. for 2 min, and further at 74° C. for 3 min per cycle) with white colony suspension of above transformants. The amplified DNA fragment was then fractionated on 0.8% Agarose gel (Dojindo Laboratories). The clone showed about 1.1 kb DNA fragment amplification was selected for further experiment (pBICR16G6PT Δ G). The bacterial clone harboring pBICR16G6PT Δ G vector was cultured over night at 37° C. with 2 ml of LB medium including 50 μg/ml of kanamycin. Then, pre-culture was inoculated to the 500 ml of LB medium including 50 μg/ml of kanamycin and cultured over night at 37° C. The bacterial cell was collected by centrifugation at 8000 rpm for 10 minutes and the vector DNA was purified using QIAGEN plasmid purification kit (QIAGEN, Inc.).

The hereinabove mentioned oligonucleotide U is represented by SEQ ID No:26 and the oligonucleotide K is represented by SEQ ID No:19.

(2) Confirmation of GUS Gene Expression by the Gene Bombardment pBICR16G6PT Δ G was introduced to the soybean somatic embryo using the method by Morikawa et. al. (C.M.Particle Gun System, Rehbock Co., Tokyo, Japan) as described Example 5. For the control experiment, pBI221 (Clontech Laboratories, Inc.) was introduced in the same way. Bombarded soybean somatic embryo were left at 25° C. for 24 hr and soaked with GUS staining buffer at 37° C. for over night. Strong GUS staining pattern were observed in the soybean somatic embryo which was bombarded with pBICR16G6PT Δ G.

Example 8

Introduction of Mutation Site to a Promoter of the Present Invention (1) Introduction of Mutation Site to the Promoter (1-1) Deletion of Sac I Recognition Site in a Promoter of the Present Invention Two μg of pBICR16G6P is treated with 20U of Sac I to digest it completely. Then, this DNA fragment is further treated with 5U of T4 DNA polymerase (Takara Shuzo Co., Ltd.) to make blunt ends and phenol treatment and ethanol precipitation are then conducted as described above to recover the DNA fragment. This DNA fragment can be then fractionated on 1.0% Agarose gel (Dojindo Laboratories) and the DNA bands of about (a) 3.9 kb and (b) 880 bp in size are excised, and the DNA fragments, (a) and (b) in the sections are purified using glass beads (Bio-Rad Laboratories). Fifty ng of DNA fragment (a) and 100 ng of DNA fragment (b) are subjected to ligation reaction using a ligation kit, the ligate is introduced into competent cells of *E. coli* strain JM109 (Takara Shuzo Co., Ltd.), and the transformed bacterial cell is cultured on LB medium containing 100 μg/ml of ampicillin for over night.

The hereinbelow mentioned oligonucleotide M is represented by SEQ ID No:27 and the oligonucleotide G is represented by SEQ ID No:15.

Oligonucleotides M and G having the following nucleotide sequences that contain nucleotide sequence as described above:

oligonucleotide M: 5'-GTAAA ACGAC GGCCA GT-3' (17mer)

oligonucleotide G: 5'-GGAAG CTTCA TGTGT GCCCT ACAGC ACA-3'(28mer)

are synthesized and used as primers to conduct PCR (40 cycle of incubation at 94° C. for 1 min, then at 55° C. for 2 min, and further at 74° C. for 3 min per cycle) with grown colony suspension of above transformants. The amplified DNA fragment is then fractionated on 0.8% Agarose gel (Dojindo Laboratories). The clone shows about 2 kb DNA fragment amplification is selected and the plasmid DNA is purified using Qia-prep spin kit (QIAGEN, Inc.). The purified plasmid DNAs are cleaved with Sac I and analyze by 1.0% agarose gel electrophoresis to select a plasmid that loses the Sac I recognition site. The gene nucleotide sequence shown in SEQ ID No.3 is a example of the plasmid that loses the Sac I recognition site.

(1-2) Deletion of Sph I Recognition Site in a Promoter of the Present Invention

As described in section (1-1), Sph I recognition site in the DNA fragment shown in SEQ ID No.7 can be deleted. Two µg of pBICR16G6P is treated with 20U of Sph I to digest it completely. Then, this DNA fragment is further treated with 5U of T4 DNA polymerase (Takara Shuzo Co., Ltd.) to make blunt ends and phenol treatment and ethanol precipitation are then conducted as described above to recover the DNA fragment. This DNA fragment can be then fractionated on 0.8% Agarose gel (Dojindo Laboratories) and the DNA bands of about (c) 3.0 kb and (d) 1.6 kb in size are excised, and the DNA fragments, (c) and (d) in the sections are purified using glass beads (Bio-Rad Laboratories). Fifty ng of DNA fragment (c) and 100 ng of DNA fragment (d) are subjected to ligation reaction using a ligation kit, the ligate is introduced into competent cells of *E. coli* strain JM109 (Takara Shuzo Co., Ltd.), and the transformed bacterial cell is cultured on LB medium containing 100 µg/ml of ampicillin for over night.

The hereinbelow mentioned oligonucleotide M is represented by SEQ ID No:27 and the oligonucleotide N is represented by SEQ ID No:28.

Oligonucleotides M and N having the following nucleotide sequences that contain nucleotide sequence as described above:

oligonucleotide M: 5'-GTAAA ACGAC GGCCA GT-3' (17mer)

oligonucleotide N: 5'-AGGAC GACTT AGGTG AATAC-3'(20mer)

are synthesized and used as primers to conduct PCR (40 cycle of incubation at 94° C. for 1 min, then at 55° C. for 2 min, and further at 74° C. for 3 min per cycle) with grown colony suspension of above transformants. The amplified DNA fragment is then fractionated on 0.8% Agarose gel (Dojindo Laboratories). The clone shows about 1.6 kb DNA fragment amplification is selected and the plasmid DNA is purified using Qia-prep spin kit (QIAGEN, Inc.). The purified plasmid DNAs are cleaved with Sph I and analyzed by 1.0% agarose gel electrophoresis to select a plasmid that loses the Sph I recognition site. The gene nucleotide sequence shown in SEQ ID No.4 is a example of the plasmid nucleotide sequence that lost the Sph I recognition site. Also the promoter which loses the Sph I recognition site can be used to further delete the Sac I recognition site as described in section (1-1).

(1-3) Deletion of Xba I Recognition Site in Promoter of the Present Invention

As described in section (1-1) and (1-2), Xba I recognition site in the DNA fragment shown in SEQ ID No.7 can be deleted. Two µg of pBICR16G6P is treated with 20U of Xba I to digest it completely. Then, this DNA fragment is further treated with 5U of T4 DNA polymerase (Takara Shuzo Co., Ltd.) to make blunt ends and phenol treatment and ethanol precipitation are then conducted as described above to recover the DNA fragment. This DNA fragment can be then fractionated on 0.8% Agarose gel (Dojindo Laboratories) for the DNA bands of about (e) 7.0 kb in size and on 4.0% Nusieve Agarose (FMC BioProducts) for the DNA band of (f) 250 bp in size. The DNA fragments in the section are purified using glass beads (Bio-Rad Laboratories). Fifty ng of DNA fragment (e) and 20 ng of DNA fragment (f) are subjected to ligation reaction using a ligation kit, the ligate is introduced into competent cells of *E. coli* strain JM109 (Takara Shuzo Co., Ltd.), and the transformed bacterial cell is cultured on LB medium containing 100 µg/ml of ampicillin for over night.

The hereinbelow mentioned oligonucleotide M is represented by SEQ ID No:27 and the oligonucleotide N is represented by SEQ ID No:28.

Oligonucleotides M and N having the following nucleotide sequences that contain nucleotide sequence as described above:

oligonucleotide M: 5'-GTAAA ACGAC GGCCA GT-3' (17mer)

oligonucleotide O: 5'-ATACA TCTTT TCAAA TTTCA-3' (20mer)

are synthesized and used as primers to conduct PCR (40 cycle of incubation at 94° C. for 1 min, then at 55° C. for 2 min, and further at 74° C. for 3 min per cycle) with grown colony suspension of above transformants. The amplified DNA fragment is then fractionated on 4.0% Nusieve Agarose gel (FMC BioProducts). The clone shows about 250 bp DNA fragment amplification is selected and the plasmid DNA is purified using Qia-prep spin kit (QIAGEN, Inc.). The purified plasmid DNAs are cleaved with Xba I and analyze by 1.0% agarose gel electrophoresis to select a plasmid that loses the Xba I recognition site. The gene nucleotide sequence shown in SEQ ID No.5 is a example of the plasmid nucleotide sequence that loses the Xba I recognition site. Also the promoter which loses the Xba I recognition site can be used to further deletion of the Sac I recognition site or Sph I recognition site as described in section (1-1) or (1-2), respectively.

(2) Construction of a Plant Expression Vector Containing a Mutated Promoter of the Present Invention The hereinbelow mentioned oligonucleotide G is represented by SEQ ID No:15 and the oligonucleotide H is represented by SEQ ID No:16.

The expression vector can be constructed by the method described in Example 2. Oligonucleotides G and H having the following nucleotide sequences that contain restriction enzyme-recognition nucleotide sequences for cloning:

oligonucleotide G: 5'-GGAAG CTTCA TGTGT GCCCT ACAGC ACA-3' (28 mer)

oligonucleotide H: 5'-GGTCT AGAGA TCTTT AGAAT GTGAT TGCTG-3' (30 mer), are synthesized and used as primers to conduct PCR (40 cycle of incubation at 94° C. for 1 min, then at 55° C. for 2 min, and further at 74° C. for 3 min per cycle) using, as a template, the plasmid having the nucleotide sequence shown in SEQ ID No: 3,4 or 5. The amplified DNA fragment is treated with 10 U of Hind III and 10 U of Xba I to digest it completely, and part of the digest is then fractionated on 0.8% agarose gel. The DNA band of about 2.0 kb in size or the DNA bands of about 1.7 kb and 250 bp are excised respectively, and DNA fragments contained in the sections are purified using glass beads (Bio-Rad Laboratories). Two µg of vector pIG121HM (see FIG. 3), which is derived from pBIN19 described in, e.g., Ohta, S. et al., Plant Cell Physiol. 31(6):805–813 (1990) and Hiei, Y. et al., Plant J. 6:271–282 (1994), is digested with 10 U of Hind III and 10 U of Xba I, and further treated with alkaline phosphatase to conduct dephosphorylation. Phenol treatment and ethanol precipitation are then conducted as described above to recover the vector DNA. After the vector DNA and the above two DNA fragments (about 2.0 kb, 1.7 kb and about 250 bp) are subjected to ligation reaction using a ligation kit, the ligate is introduced into competent cells of *E. coli* strain HB101 (Takara Shuzo Co., Ltd.), and the bacterial strain which has gone through the introduction steps is cultured on LB medium containing 50 µg/ml kanamycin. Vector DNAs are then prepared from growing clones, cleaved with restriction enzymes Hind III and Xba I, and analyzed by agarose gel electrophoresis to select a vector that contained 2.0 kb or 1.7 kb and 250 bp DNA fragments described above. Furthermore, using the selected vector as a template, PCR (40 cycles of incubation at 94° C. for 1 min, then at 55° C. for 2 min, and further at 74° C. for 3 min per cycle) is conducted using the aforementioned oligonucleotides G and H as primers:

oligonucleotide G: 5'-GGAAG CTTCA TGTGT GCCCT ACAGC ACA-3' (28 mer)

oligonucleotide H: 5'-GGTCT AGAGA TCTTT AGAAT GTGAT TGCTG-3' (30 mer):

As a result, it is confirmed that a DNA fragment about 2 kb is amplified, and Ti plasmid expression vectors containing a promoter having the nucleotide sequence shown in SEQ ID 3, 4 or 5 of the present invention upstream from β-glucuronidase gene are thus obtained. Furthermore, NOS terminator contained in the above mentioned plasmids can be exchanged with the terminator derived from pBICR16G6PT or pBICR16G6PT Δ described in Example 6.

Example 9

Construction of Vector Containing Promoter and Terminator of the Present Invention and Confirmation of Expression of Transgene (1) Introduction of GUS Gene to the Expression Vector Containing the Terminator of Present Invention GUS gene can be introduced to the expression vector as described Example 7(1). Two µg of pBI221 plasmid DNA (Clontech Laboratories, Inc.) is treated with 20U of Sma I and 20U of Sac I to digest it completely and recovered DNA by the ethanol precipitation. Then, this DNA fragment is treated with 5U of T4 DNA polymerase (Takara Shuzo Co., Ltd.) to make blunt ends and phenol treatment and ethanol precipitation are then conducted as described above to recover the DNA fragment. DNA fragment is then fractionated on 1.0% Agarose gel (Dojindo Laboratories). The DNA band of about 1.7 kb in size is excised, and GUS gene contained in the section is purified using glass beads (Bio-Rad Laboratories). Also two µg of pBluescript KS vector (Clontech Laboratories, Inc.) is treated with 20U of Sma I to digest it completely and further treated with alkaline phosphatase to conduct dephosphorylation. Phenol treatment and ethanol precipitation are then conducted as described above to recover the vector DNA fragment. Fifty µg of vector DNA and 100 ng of above 1.7 kb GUS gene fragment is subjected to ligation reaction using a ligation kit, the ligate is introduced into competent cells of *E. coli* strain JM109 (Takara Shuzo Co., Ltd.), and the transformed bacterial cell is cultured on LB medium containing 100 µg/ml of ampicillin and 40 µg/ml of X-Gal.

The hereinbelow mentioned oligonucleotide M is represented by SEQ ID No:27 and the oligonucleotide K is represented by SEQ ID No:19.

Oligonucleotides M and K having the following nucleotide sequences that contain nucleotide sequence based on pBluescript KS (oligonucleotide K) and GUS gene (oligonucleotide M):

oligonucleotide M: 5'-GTAAA ACGAC GGCCA GT-3' (17mer)

oligonucleotide K: 5'-ACATG TGGAG TGAAG AGTAT-3' (21mer)

are synthesized and used as primers to conduct PCR (40 cycle of incubation at 94° C. for 1 min, then at 55° C. for 2 min, and further at 74° C. for 3 min per cycle) with white colony suspension of above transformants. The amplified DNA fragment is then fractionated on 4.0% Nusieve Agarose gel (FMC BioProducts). The clone shows the 410 bp DNA fragment amplification is selected for further construction. Two µg of purified plasmid DNA is treated with 20U of Sal I and 20U of BamH I to digest it completely and DNA fragment is then fractionated on 0.8% Agarose gel (Dojindo Laboratories). The DNA band of about 1.7 kb in size is excised, and DNA fragment contained in the section is purified using glass beads (Bio-Rad Laboratories). Two µg of pBICR16G6PT is digested with 20U of Sal I and 20U of BamH I and further treated with alkaline phosphatase to conduct dephosphorylation (Takara Shuzo Co., Ltd.). Fifty ng of vector DNA and 20 ng of above 1.7 kb DNA fragment are subjected to ligation reaction using a ligation kit, the ligate is introduced into competent cells of *E. coli* strain HB101 (Takara Shuzo Co., Ltd.), and the transformed bacterial cell is cultured on LB medium containing 50 µg/ml of kanamycin.

The hereinbelow mentioned oligonucleotide U is represented by SEQ ID No:26 and the oligonucleotide K is represented by SEQ ID No:19.

Oligonucleotides U and K having the following nucleotide sequences as described:

oligonucleotide U: 5'-GGGAA TTCCT GAAAA GGAAG TTCAT CGATC TATC-3'(34mer)

oligonucleotide K: 5'-ACATG TGGAG TGAAG AGTAT-3' (21mer)

are synthesized and used as primers to conduct PCR (40 cycle of incubation at 94° C. for 1 min, then at 55° C. for 2 min, and further at 74° C. for 3 min per cycle) with white colony suspension of above transformants. The amplified DNA fragment is then fractionated on 0.8% Agarose gel (Dojindo Laboratories). The clone shows about 1.1 kb DNA fragment amplification is selected for further experiment (pBICR16G6PTG). The bacterial clone harboring pBICR16G6PTG is pre-cultured over night at 37° C. with 2 ml of LB medium including 50 µg/ml of kanamycin. Then, pre-culture is inoculated to the 500 ml of LB medium including 50 µg/ml of kanamycin and cultured over night 37° C. The bacterial cell is collected by centrifugation at 8000 rpm for 10 minutes and the plasmid DNA is purified using QIAGEN plasmid purification kit (QIAGEN, Inc.). The promoter of the present invention in SEQ ID No.7 contained in pBICR16G6PTG or pBICR16G6PT Δ G can be exchanged with the promoters described in Example 8, cauliflower mosaic virus 35S promoter (Nature, 313:810–812) or NOS promoter (Nucleic Acid Research, 11(2):369–385 (1983)).

(2) Confirmation of GUS Gene Expression Using Transgenic Tobacco

As described in Example 2 (2), a section of sterile-cultured tobacco leaf (0.7-cm square) is immersed for 2 minutes in *Agrobacterium* culture containing expression vector described in Example 8 and 9 cultured overnight at 30° C. in YEB liquid medium containing 50 µg/ml kanamycin, and after removing excess liquid with sterile filter paper, placed on MS-NB medium. After cocultivation for 5 days at 25° C. under the conditions of 16 hours light and 8 hours dark, the section is washed with MS liquid medium, and placed on MS-NBC medium. After culturing for additional 5 days, the section is transferred onto MS-NBCK medium containing a selection drug, and stationally culture for about one month. The regenerated shoot is cut from the leaf section, and subcultured on MS-CK medium. After about one month, the individuals that rooted are planted on soil to obtain self-pollinated seeds. GUS gene can be confirmed in above transgenic Tobacco genome as described in Example 3. Also GUS expression activity based on a terminator of the present invention can be confirmed by the method described in Example 4.

(3) Confirmation of GUS Gene Expression Using the Gene Bombardment

The vector DNAs can be introduced to the soybean somatic embryo using the method by Morikawa et. al. (C.M.Particle Gun System, Rehbock Co., Tokyo, Japan) as described Example 5. For the control experiment, pBI221 (Clontech Laboratories, Inc.) can be introduced in the same way. Bombarded soybean somatic embryo are left at 25° C. for 24 hr and soaked with GUS staining buffer at 37° C. for over night. Strong GUS staining pattern are observed in the soybean somatic embryo which is bombarded by above mentioned vectors.

The compositions of mediums used in Examples were as follows:

(1) Media for Plant (i) MS Agar Medium (for Tobacco)

4.4 g MURASHIGE AND SKOOG BASAL MEDIUM (Sigma Chemical Co.) and 30 g sucrose were dissolved in 1 L distilled water, adjusted to pH 5.8 with 1 N KOH, supplemented with 8 g agar (Wako Pure Chemical Industries, Ltd.), and then autoclaved.

(ii) MS-NB Agar Medium

MS agar medium supplemented with 0.1 µg/ml 1-naphthaleneacetic acid (NAA), 1.0 µg/ml 6-benzylaminopurine (BA)

(iii) MS-NBC Agar Medium

MS-NB agar medium supplemented with 300 µg/ml Cefotaxime (iv) MS-NBCK Agar Medium MS-NB agar medium supplemented with 100 µg/ml kanamycin and 300 µg/ml Cefotaxime (v) MS-CK Agar Medium MS agar medium supplemented with 100 µg/ml kanamycin and 300 µg/ml of Cefotaxime (vi) MS Agar Medium (for *Arabidopsis*)

4.4 g MURASHIGE AND SKOOG (Sigma Chemical Co.) and 20 g sucrose were dissolved in 1 L distilled water, adjusted to pH 6.3 with 1 N KOH, supplemented with 2 g Gellan gun (Wako Pure Chemical Industries, Ltd.), and then autoclaved.

(vii) CIM Agar Medium

MS agar medium supplemented with 0.5 µg/ml 2,4-dichlorophenoxyacetic acid (2,4-D), 0.05 µg/ml kinetin (viii) SIMC Agar Medium MS agar medium supplemented with 5 µg/ml $N_6$-[2-isopentenyl]adenin (2-iP), 0.15 µg/ml indoleacetic acid (IAA), 300 µg/ml Cefotaxime (ix) SIMCH Agar Medium SIMC agar medium supplemented with 20 µg/ml hygromycin (2) Media for Bacteria and Phages (i) L-Medium 10 g Bacto-trypton (Difco Laboratories), 5 g Bacto-yeast extract (Difco Laboratories) and 10 g NaCl are dissolved in 1 L distilled water, adjusted to pH 7.0 with 5 N NaOH, and autoclaved. When used for plates, 15 g agar is added thereto before autoclaving.

(ii) YEB Medium 5 g Bacto-beef extract (Difco Laboratories), 1 g Bacto-yeast extract (Difco Laboratories), 5 g polypeptone, 5 g sucrose, 0.2 ml 10 N NaOH are dissolved in 1 L distilled water, autoclaved, and then supplemented with 0.2 ml filter-sterilized 1M $MgSO_4$ before use. For preparing the agar medium, 15 g agar is added thereto before autoclaving.

EFFECTS OF THE INVENTION

According to the present invention, promoters and terminators capable of efficiently expressing a gene of interest in plants are provided.

The invention claimed is:

1. An isolated promoter comprising the following DNA (a) or (b), characterized in that said promoter is capable of functioning in plant cells:
   (a) DNA comprising the nucleotide sequence shown in SEQ ID NO:1, or
   (b) DNA having promoter functions equivalent to those of the above DNA (a) and comprising a modified nucleotide sequence in which one or more bases are deleted, substituted, or added in the nucleotide sequence shown in SEQ ID NO:1, and wherein:
      (i) said modified nucleotide sequence has more than 90% identity to the nucleotide sequence of any region consisting of 250 bp or more within the nucleotide sequence shown in SEQ ID NO:1,
      (ii) said modified nucleotide sequence contains the nucleotide sequence shown in SEQ ID NO:24, and
      (iii) said modified nucleotide sequence hybridizes to the nucleotide sequence shown in SEQ ID NO:1 under conditions that include washing in 300 mM sodium chloride, 30 mM sodium citrate, and 1% SDS at 55° C.

2. A chimeric gene comprising the isolated promoter of claim 1 and a desired coding sequence operatively linked to each other.

3. A chimeric gene comprising the isolated promoter of claim 1, a desired coding sequence, and a terminator that is capable of functioning in plant cells operatively linked to each other.

4. A vector comprising the promoter of claim 1 and a desired coding sequence.

5. A vector comprising the promoter of claim 1, a desired coding sequence, and a terminator that is capable of functioning in plant cells.

6. An isolated promoter capable of functioning in plant cells in accordance with claim 1, wherein the promoter comprises the DNA (a).

7. An isolated promoter capable of functioning in plant cells in accordance with claim 1, wherein the promoter comprises the DNA (b).

8. A vector comprising the isolated promoter according to claim 1.

9. An isolated promoter comprising the following DNA (a) or (b), and characterized in that said promoter is capable of functioning in plant cells:
   (a) DNA comprising the nucleotide sequence shown in SEQ ID NO:1, or
   (b) DNA having promoter functions equivalent to those of the above DNA (a) and comprising a modified nucleotide sequence in which one or more bases are deleted, substituted, or added in the nucleotide sequence shown in SEQ ID NO: 1, and wherein:
      (i) said modified nucleotide sequence contains the nucleotide sequence shown in SEQ ID NO:24, and
      (ii) said modified nucleotide sequence hybridizes to the nucleotide sequence shown in SEQ ID NO:1 under conditions that include washing in 300 mM sodium chloride, 30 mM sodium citrate, and 1% SDS at 55° C.

10. A method of producing a transformant comprising introducing into a host cell any one of: a) the promoter of claim 1; b) the chimeric gene of claim 2 or 3; or c) the vector of claim 4 or 8.

11. A non-human transformant comprising any one of: a) the promoter of claim 1; b) the chimeric gene of claim 2 or 3; or c) the vector of claim 4 or 8, introduced into a host cell.

12. The transformant of claim 11, wherein the host cell is a microbial cell or a plant cell.

13. A chimeric gene comprising the isolated promoter of claim 9 and a desired coding sequence operatively linked to each other.

14. A chimeric gene comprising a) the isolated promoter of claim 9, b) a desired coding sequence, and c) a terminator that is capable of functioning in plant cells, wherein a), b) and c) are operatively linked to each other.

15. A vector comprising the promoter of claim 9 and a desired coding sequence.

16. A vector comprising the promoter of claim 9, a desired coding sequence, and a terminator that is capable of functioning in plant cells.

17. An isolated promoter capable of functioning in plant cells in accordance with claim 9, wherein the promoter comprises the DNA (b).

18. A vector comprising the isolated promoter according to claim 9.

19. A method of producing a transformant comprising introducing into a host cell any one of: a) the promoter of claim 9; b) the chimeric gene of claim 13 or 14; or c) the vector of claim 15 or 18.

20. A non-human transformant comprising any one of: a) the promoter of claim 9; b) the chimeric gene of claim 13 or 14; or c) the vector of claim 15 or 18, introduced into a host cell.

21. The transformant of claim 20, wherein the host cell is a microbial cell or a plant cell.

* * * * *